(12) United States Patent
Jarrell et al.

(10) Patent No.: US 7,981,685 B2
(45) Date of Patent: Jul. 19, 2011

(54) GENERATION OF ACYL AMINO ACIDS

(75) Inventors: Kevin A. Jarrell, Lincoln, MA (US); Prashanth Vishwanath, Brighton, MA (US); Gabriel Reznik, Brookline, MA (US)

(73) Assignee: Modular Genetics, Inc., Woburn, MA (US)

( * ) Notice: Subject to any disclaimer, the term of this patent is extended or adjusted under 35 U.S.C. 154(b) by 0 days.

(21) Appl. No.: 12/596,272

(22) PCT Filed: Apr. 16, 2008

(86) PCT No.: PCT/US2008/060474
§ 371 (c)(1),
(2), (4) Date: Jun. 29, 2010

(87) PCT Pub. No.: WO2008/131002
PCT Pub. Date: Oct. 30, 2008

(65) Prior Publication Data
US 2011/0030102 A1 Feb. 3, 2011

Related U.S. Application Data

(60) Provisional application No. 60/923,679, filed on Apr. 16, 2007, provisional application No. 61/026,610, filed on Feb. 6, 2008.

(51) Int. Cl.
*C12P 13/16* (2006.01)
*C12P 13/04* (2006.01)

(52) U.S. Cl. ........................................ 436/112; 435/106

(58) Field of Classification Search .................. None
See application file for complete search history.

(56) References Cited

U.S. PATENT DOCUMENTS

| | | | |
|---|---|---|---|
| 5,652,116 A | 7/1997 | Grandi et al. | |
| 5,795,738 A | 8/1998 | Grandi et al. | |
| 6,060,051 A | 5/2000 | Heins et al. | |
| 6,103,228 A | 8/2000 | Heins et al. | |
| 6,291,426 B1 | 9/2001 | Heins et al. | |
| 6,417,163 B1 | 7/2002 | Heins et al. | |
| 6,638,910 B2 | 10/2003 | Heins et al. | |
| 2010/0297751 A1* | 11/2010 | Marahiel et al. | 435/320.1 |

OTHER PUBLICATIONS

Steller et al. Initiation of Surfactin Biosynthesis and the Role of the SrfD-Thioesterase Protein. Biochem. 43: 11331-11343, 2004.*
Assie et al., "Insecticide activity of surfactins and iturins from a biopesticide *Bacillus subtilis* Cohn (S499 strain)" *Meded Rijksuvin Gent Fak Landbouwkd Toegep Biol Wet.*, 67(3):647-655 (2002) Abstract only.
ATCC8185 http://www.atcc.org/ATCCAdvancedCatalogSearch/ProductDetails/tabid/452/Default.aspx?ATCCNum=8185&Template=bacteria.

Bruner et al., "Structural Basis for the Cyclization of the Lipopeptide Antibiotic Surfactin by the Thioesterase Domain SrfTE" *Structure*, 10:301-310 (2002).
Coque et al., "The Cephamycin Biosynthetic Genes *pcbAB*, Encoding a Large Multidomain Peptide Synthetase, and *pcbC* of *Nocardia lactamdurans* are Clustered Together in an Organization Different from the Same Genes in *Acremonium chrysogenum* and *Penicillium chrysogenum*," *Mol. Microbiol.* 5:1125, 1991.
Cosmina et al., "Sequence and Analysis of the Genetic Locus Responsible for Surfactin Synthesis in *Bacillus subtilis*," *Mol. Microbiol.* 8 (5) 821, 1993.
de Ferra et al., "Engineering of Peptide Synthetases," *Journal of Biological Chemistry* 272:40, 25304-25309, 1997.
Diez et al., "The cluster of penicillin biosynthetic genes. Identification and characterization of the pcbAB gene encoding the alpha-aminoadipyl-cysteinyl-valine synthetase and linkage to the pcbC and penDE genes," *J. Biol. Chem.* 265(27):16358-16365, 1990.
Fields et al., "A Novel Genetic System to Detect Protein-Protein Interactions," *Nature* 340:245-6, 1989.
International Preliminary Report on Patentability from PCT/US08/060474, dated Oct. 20, 2009.
International Search Report from PCT/US08/60474, dated Oct. 21, 2008.
Kleinkauf et al., "Biosynthesis of Peptide Antibiotics," *Annu. Rev. Microbiol.*, 41:259-289, 1987.
Krätzxchmar et al., "Gramicidin S Biosynthesis Operon Containing the Structural Genes *grsA* and *grsB* Has an Open Reading Frame Encoding a Protein Homologous to Fatty Acid Thioesterases," *J. Bacteriol.* 171 (10) 5422-5429, 1989.
Lait et al., "Rapid biosynthesis of N-linolenoyl-L-glutamine, an elicitor of plant volatiles, by membrane-associated enzyme(s) in *Manduca sexta*" *PNAS USA*, 100(12):7027-7032 (2003).
MacCabe et al., "δ-(L-α-Aminoadipyl)-L-Cysteinyl-D-Valine Synthetase from *Aspergillus nidulans*," *J. Biol. Chem.* 266:12646, 1991.
Nagai et al., "Study on Surfactin, A Cyclic Depsipeptide. II. Synthesis of Surfactin $B_2$ Produced by *Bacillus natto* KMD 2311," *Chem Pharm Bull* (Tokyo) 44 (1) 5-10, 1996.
Richardt et al., "Ebony, a Novel Nonribosomal Peptide Synthetase for Beta-Alanine Conjugation with Biogenic Amines in *Drosophila*," *J. Biol. Chem.*, 278(42):41160-41166, 2003.
Smith et al., "The Multifunctional Peptide Synthetase Performing the First Step of Penicillin Biosynthesis in *Penicillium chrysogenum* is a 421 073 Dalton Protein Similar to *Bacillus brevis* Peptide Antibiotic Synthetases," *EMBO J.* 9 (9) 2743-2750, 1990.
Smith et al., "β-Lactam Antibiotic Biosynthetic Genes Have Been Conserved in Clusters in Prokaryotes and Eukaryotes," *EMBO J.* 9 (3) 741-747, 1990.
Written Opinion of the ISA from PCT/US08/60474, dated Oct. 21, 2008.

* cited by examiner

*Primary Examiner* — Michele Joike
(74) *Attorney, Agent, or Firm* — Choate, Hall & Stewart, LLP; Atsuko N. Polzin

(57) ABSTRACT

Engineered polypeptides useful in synthesizing acyl amino acids are provided. Also provided are methods of making acyl amino acids using engineered polypeptides. In certain embodiments, an acyl amino acid produced using compositions and/or methods of the present invention comprises cocoyl glutamate.

3 Claims, 18 Drawing Sheets

FIG. 7 Titer of cultures used to produce FA-GLU using OKB105 Δ(upp)Spect^R FA-GLU-TE-MG

| 070814-16 | 3071651 | 7062974 | 78886866 | 42889261 | 18145721 | 150056473 | 306237700 | 301880567 | average of injections - 09 and - 16 |
| 070814-22 | 2033339 | 5413458 | 72306356 | 36304879 | 16649341 | 132707373 | 270831373 | 28854537 | average of injections - 16 and - 22 |
| 070814-28 | 1973150 | 4941738 | 65886895 | 36884924 | 15963142 | 125649849 | 256428263 | 263629818 | average of injections - 22 and - 28 |

| | FA-Glu removed from liquid | | | | Total amount based on total volume isolated (multiply by [11ml x 20 (1 liter) liquid] and by [5 x 20] (1 liter) cells) | Conditions used to obtain results. Day 0 refers to time when some cultures were supplemented) | | Growth Conditions used to obtain results | Total titer from liquid and cells |
|---|---|---|---|---|---|---|---|---|---|
| samples | area m/z 387 | ug injected | ug/sample | | | | | | |
| 024415 | 119193475 | 0.285 | 28.49 | | 6.26 mg | Day 0 (0 supplementation) | | Day 0 (0 supplementation) | 9.67 mg |
| 024416 | 70450505 | 0.168 | 16.84 | | 3.70 mg | Day 2 (0 supplementation) | | Day 2 (0 supplementation) | 6.91 mg |
| 024417 | 66404982 | 0.220 | 22.00 | | 4.84 mg | Day 4 (0 supplementation) | | Day 4 (0 supplementation) | 8.16 mg |
| 024418 | 70635040 | 0.169 | 16.93 | | 3.72 mg | Supplemented w/0.5% Glucose | | Supplemented w/0.5% Glucose | 6.82 mg |
| 024419 | 71061800 | 0.170 | 16.98 | | 3.73 mg | Supplemented w/0.5% Glycerol | | Supplemented w/0.5% Glycerol | 6.7 mg |
| 024420 | 62167501 | 0.206 | 20.59 | | 4.52 mg | Supplemented w/Glut Acid 1mg/m | | Supplemented w/Glut Acid 1mg/m | 7.83 mg |
| 024421 | 62160546 | 0.206 | 20.59 | | 4.52 mg | Supplemented w/Tryptone 10 g/l | | Supplemented w/Tryptone 10 g/l | 7.04 mg |
| 024422 | 60485593 | 0.200 | 20.04 | | 4.40 mg | Supplemented w/Myr Acid 100ug/ml | | Supplemented w/Myr Acid 100ug/ml | 7.22 mg |
| 024423 | 60018201 | 0.199 | 19.88 | | 4.37 mg | Supplemented w/1% Soy | | Supplemented w/1% Soy | 7.28 mg |
| 024424 | 60597121 | 0.201 | 20.07 | | 4.41 mg | Suppl w/1% Soy + / 0.5 Glycerol | | Suppl w/1% Soy + / 0.5 Glycerol | 7.21 mg |

| FA-Glu recovered from cells | | | | | | | | | |
|---|---|---|---|---|---|---|---|---|---|
| 024425 | 98385502 | 0.341 | 34.10 | | 3.41 mg | Day 0 (0 supplementation) | | | |
| 024426 | 92647503 | 0.321 | 32.11 | | 3.21 mg | Day 2 (0 supplementation) | | | |
| 024427 | 95911004 | 0.332 | 33.24 | | 3.32 mg | Day 4 (0 supplementation) | | | |
| 024428 | 89413445 | 0.310 | 30.99 | | 3.09 mg | Supplemented w/0.5% Glucose | | | |
| 024429 | 85766266 | 0.297 | 29.72 | | 2.97 mg | Supplemented w/0.5% Glycerol | | | |
| 024430 | 87405819 | 0.332 | 33.15 | | 3.31 mg | Supplemented w/Glut Acid 1mg/m | | | |
| 024431 | 66450436 | 0.252 | 25.21 | | 2.25 mg | Supplemented w/Tryptone 10 g/l | | | |
| 024432 | 74526349 | 0.283 | 28.27 | | 2.82 mg | Supplemented w/Myr Acid 100ug/ml | | | |
| 024433 | 76725702 | 0.291 | 29.10 | | 2.91 mg | Supplemented w/1% Soy | | | |
| 024434 | 73875728 | 0.280 | 28.02 | | 2.80 mg | Suppl w/1% Soy + / 0.5 Glycerol | | | |

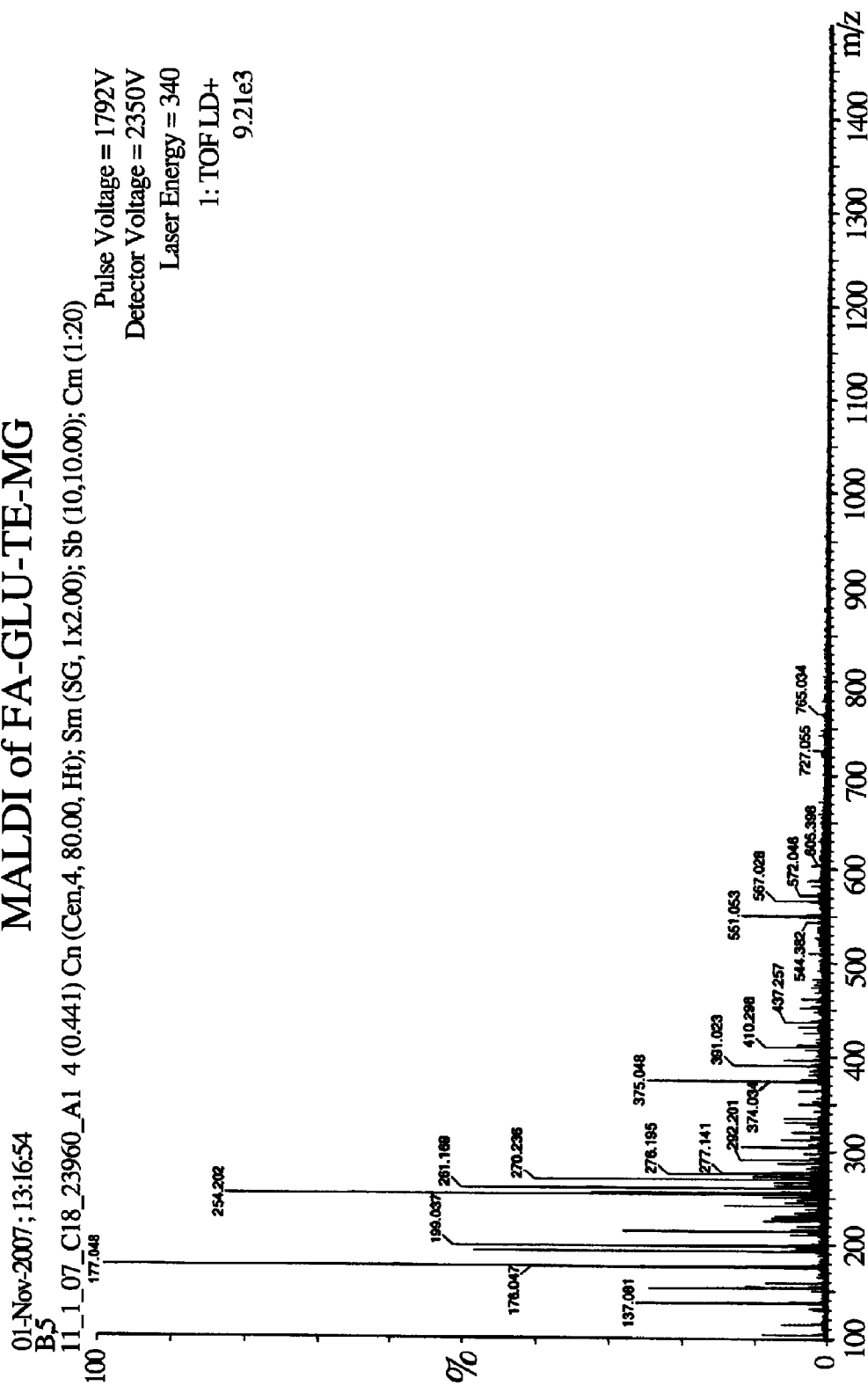

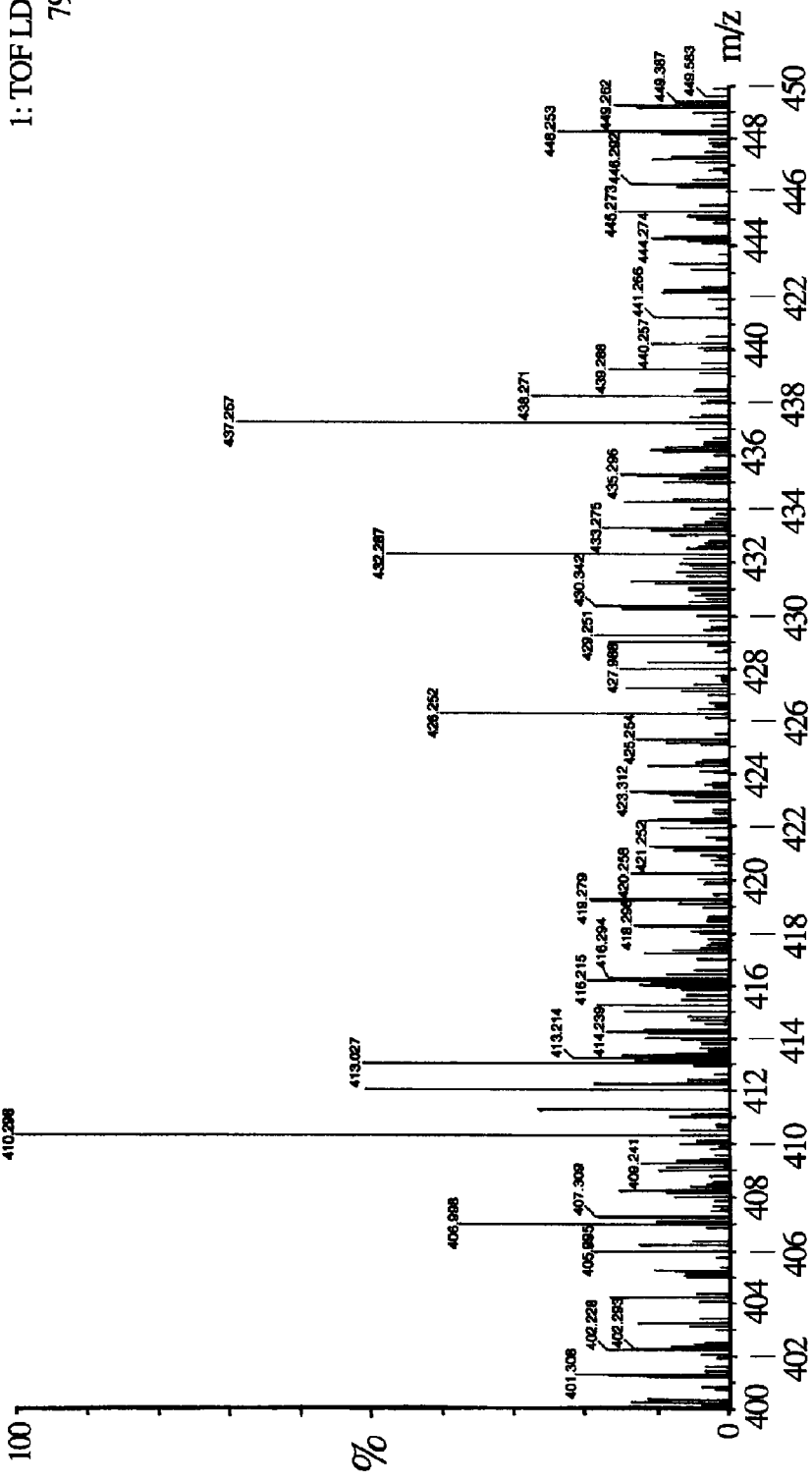
FIG. 9 Zoom of MALDI of FA-GLU-TE-MG

*FIG.11* Zoom of MALDI of FA-GLU-RED-MG

FIG. 13 Zoom of MALDI of FA-GLU-RED-MH

FIG. 15 Zoom of MALDI of FA-GLU-RED-GRN

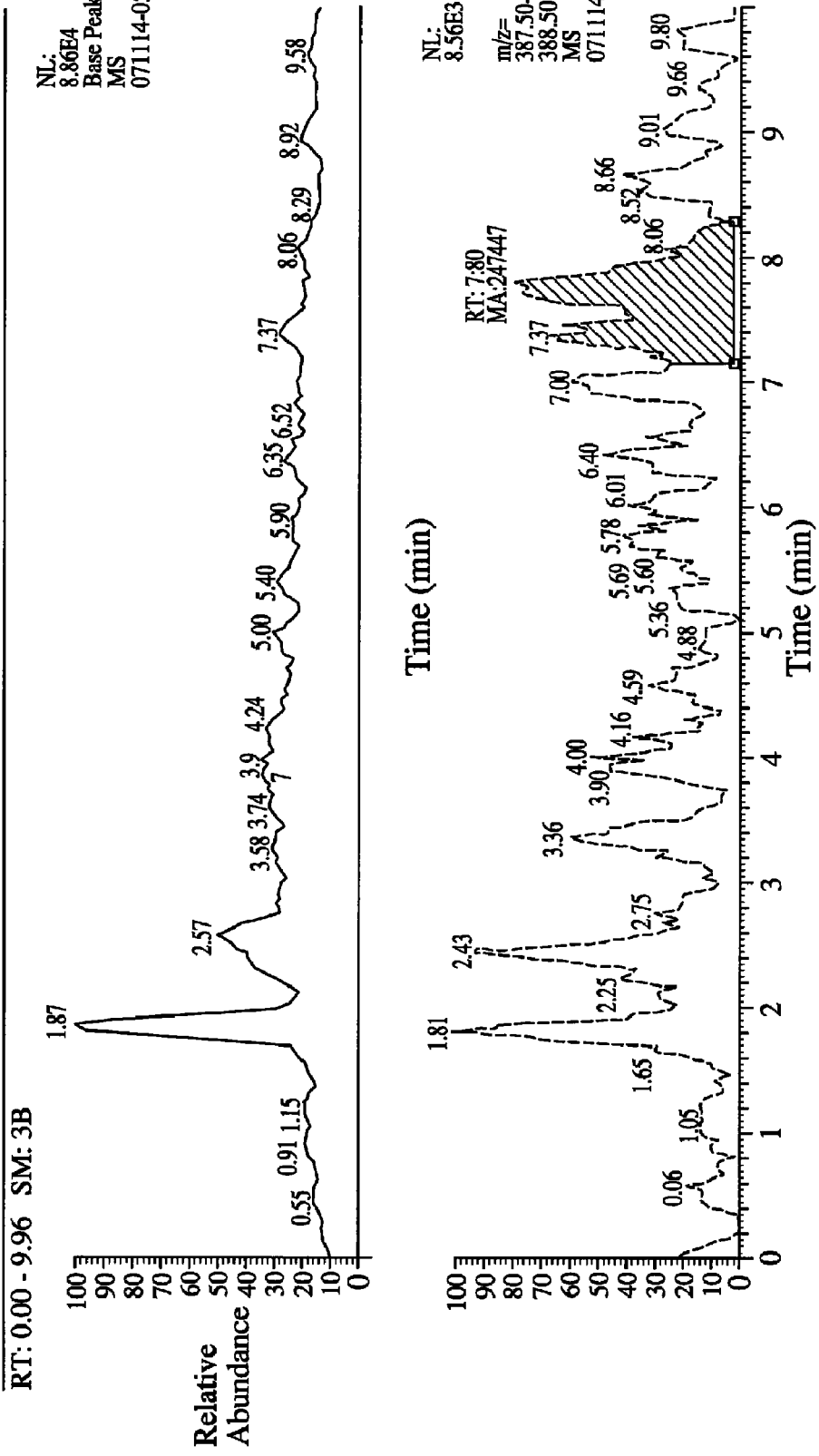
FIG. 17 MALDI of FA-GLU-RED-GRN

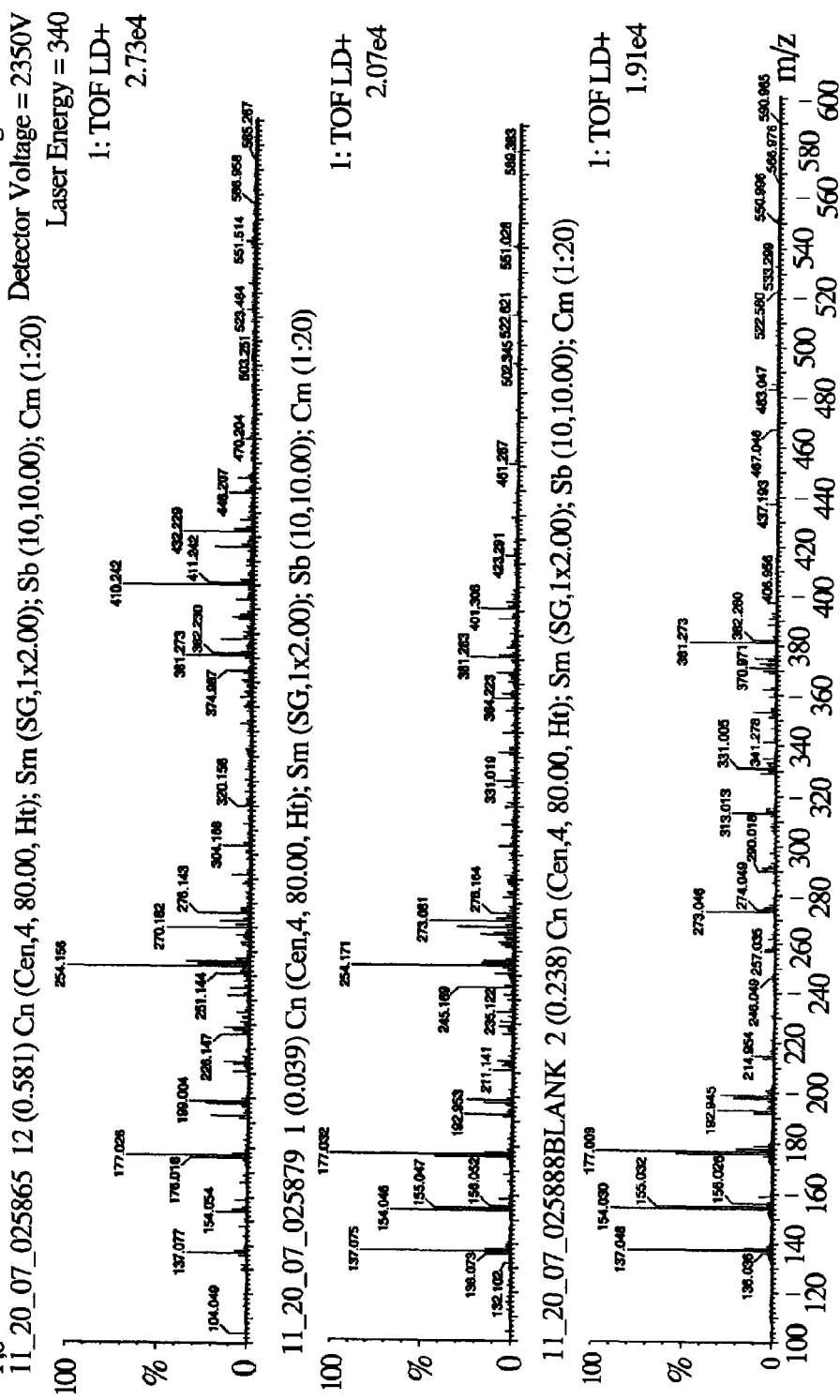
FIG. 18  MALDI ANALYSIS OF
FA-GLU-ASP-TE-MG (Top), Media w/o cells (Middle), Matrix (Bottom)

GENERATION OF ACYL AMINO ACIDS

CROSS REFERENCE TO RELATED APPLICATIONS

This application is a national phase application under 35 U.S.C. §371 of PCT International Application No. PCT/US2008/060474, filed Apr. 16, 2008, which shares at least one common inventor with, and claims priority to U.S. provisional patent application No. 60/923,679, filed Apr. 16, 2007. This application also shares at least one common inventor with, and claims priority to U.S. provisional patent application No. 61/026,610, filed Feb. 6, 2008. The entire contents of each of these applications are hereby incorporated by reference.

SEQUENCE LISTING

In accordance with 37 C.F.R. §1.52(e)(5), a Sequence Listing in the form of a text file (entitled "Sequence Listing," created on Oct. 4, 2010, and 21.1 kilobytes) is incorporated herein by reference in its entirety.

BACKGROUND

Acyl amino acids are commercially important compounds. Many have advantageous characteristics and are sold as surfactants, antibiotics, anti-insect agents and as a variety of other important agents.

Traditionally, acyl amino acids are manufactured chemically. Such chemical manufacturing methods are hampered by a variety of shortcomings including the ease of obtaining and storing the starting materials, the necessity of using harsh and sometimes dangerous chemical reagents in the manufacturing process, the difficulty and efficiency of the synthesis itself, the fiscal and environmental cost of disposing of chemical by-products, etc. Thus, new compositions and methods for the efficient and cost-effective synthesis of acyl amino acids and manufacture on a commercial scale would be beneficial.

SUMMARY OF THE INVENTION

In certain embodiments, the present invention comprises compositions and methods useful in the generation of acyl amino acids. In certain embodiments, the present invention provides an engineered polypeptide comprising a peptide synthetase domain, a fatty acid linkage domain, and a thioesterase domain. In certain embodiments, the present invention provides an engineered polypeptide comprising a peptide synthetase domain, a fatty acid linkage domain, and a reductase domain. In certain embodiments, a fatty acid linkage domain of such engineered polypeptides comprises a beta-hydroxy fatty acid linkage domain.

In certain embodiments, a peptide synthetase domain, a fatty acid linkage domain, a thioesterase domain, and/or a reductase domain of an engineered polypeptide of the present invention is a naturally occurring domain. In certain embodiments, a peptide synthetase domain, a fatty acid linkage domain, a thioesterase domain, and/or a reductase domain of an engineered polypeptide of the present invention is not naturally occurring, but it itself an engineered domain.

In certain embodiments, a peptide synthetase domain, a fatty acid linkage domain, a thioesterase domain, and/or a reductase domain of an engineered polypeptide of the present invention comprises one or more amino acid insertions, deletions, substitutions or transpositions as compared to a naturally occurring domain. In certain embodiments, a peptide synthetase domain, a fatty acid linkage domain, a thioesterase domain, and/or a reductase domain of an engineered polypeptide of the present invention exhibits homology to a naturally occurring domain. In certain embodiments, a peptide synthetase domain, a fatty acid linkage domain, a thioesterase domain, and/or a reductase domain of an engineered polypeptide of the present invention comprises an amino acid sequence that conforms to a consensus sequence of a class of naturally occurring domains.

In certain embodiments, an engineered polypeptide of the present invention produces an acyl amino acid of interest. For example, an engineered polypeptide of the present invention may produce cocoyl glutamate. Such a cocoyl glutamate-producing engineered polypeptide may comprise the first peptide synthetase domain of the first SRFA protein of the surfactin synthetase complex, the beta-hydroxy myristic acid linkage domain of the surfactin synthetase complex, and a thioesterase and/or reductase domain. Those of ordinary skill in the art will be able to use the teachings of the present invention to construct engineered polypeptides useful in the generation of any of a variety of acyl amino acids of interest. In certain embodiments, an acyl amino acid of interest is produced in a commercially useful quantity.

In certain embodiments, an engineered polypeptide of the present invention is introduced into a host cell. Useful host cells encompassed by the present invention include, without limitation, bacterial hosts such as *Bacillus subtilis*. In certain embodiments, an engineered polypeptide of the present invention is introduced into a plant cell. Transgenic plants may be produced that comprise engineered polypeptides of the present invention, which transgenic plants exhibit one or more advantageous characteristics such as, without limitation, resistance to any of a variety of insect pests.

BRIEF DESCRIPTION OF THE DRAWING

FIG. 7 shows total amount of FA-GLU compound recovered using the FA-GLU-TE-MG engineered polypeptide under various culture conditions.

FIG. 8 shows MALDI spectra analysis of FA-GLU-TE-MG.

FIG. 9 shows a close up view of the MALDI spectra analysis of FA-GLU-TE-MG shown in FIG. 8.

FIG. 17 shows MALDI spectra analysis of FA-GLU-ASP-TE.

FIG. 18 shows MALDI spectra analysis of FA-GLU-ASP-TE-MG

DESCRIPTION OF CERTAIN EMBODIMENTS

Definitions

Figure 1:
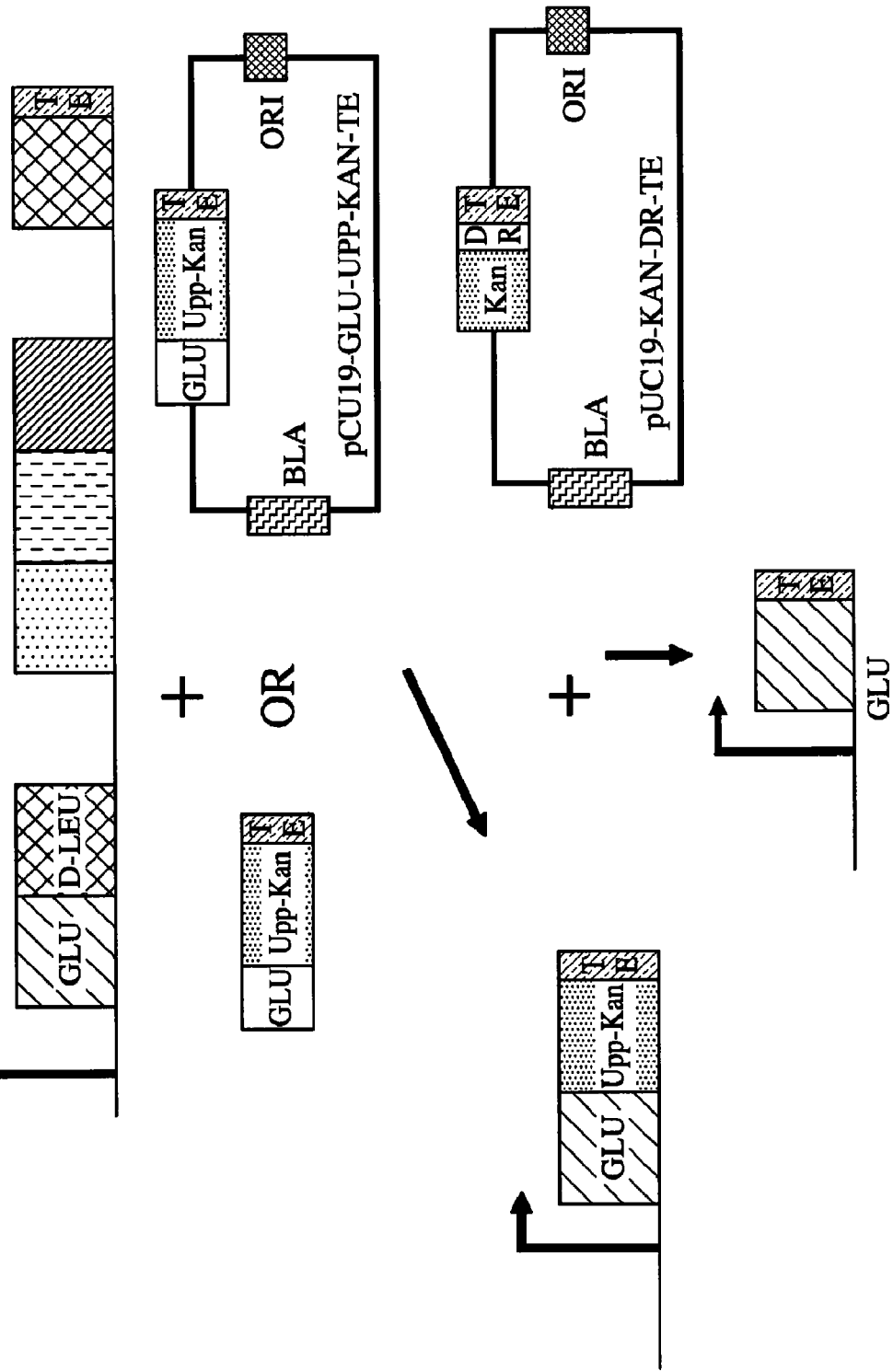
FIG. 1 shows a first embodied strategy for engineering a FA-GLU-TE construct.

Acyl amino acid: The term "acyl amino acid" as used herein refers to an amino acid that is covalently linked to a fatty acid. In certain embodiments, acyl amino acids produced by compositions and methods of the present invention comprise a beta-hydroxy fatty acid. In certain embodiments, the present invention provides compositions and methods for producing acyl amino acids by employing engineered polypeptides comprising a peptide synthetase domain covalently linked to a fatty acid linkage domain and a thioesterase domain or reductase domain. In certain embodiments, the present invention provides compositions and methods for producing acyl amino acids by employing engineered polypeptides comprising a peptide synthetase domain covalently linked to a beta-hydroxy fatty acid linkage domain and a thioesterase domain. In certain embodiments, the present invention provides compositions and methods for producing acyl amino acids by employing engineered polypeptides comprising a peptide synthetase domain covalently linked to a beta-hydroxy fatty acid linkage domain and a reductase domain. Typically, the identity of the amino acid moiety of the acyl amino acid is determined by the amino acid specificity of the peptide synthetase domain. For example, the peptide synthetase domain may specify any one of the naturally occurring amino acids known by those skilled the art to be used in ribosome-mediated polypeptide synthesis. Alternatively, the peptide synthetase domain may specify a non-naturally occurring amino acid, e.g. a modified amino acid. Similarly, the identity of the fatty acid moiety of the acyl amino acid is determined by the fatty acid specificity of the fatty acid linkage domain, such as for example a fatty acid linkage domain that is specific for a beta-hydroxy fatty acid. For example, the beta-hydroxy fatty acid may be any of a variety of naturally occurring or non-naturally occurring beta-hydroxy fatty acids. In certain embodiments, an acyl amino acid of the present invention comprises a surfactant such as, without limitation, cocoyl glutamate.

Beta-hydroxy fatty acid linkage domain: The term "beta-hydroxy fatty acid linkage domain" as used herein refers to a polypeptide domain that covalently links a beta-hydroxy fatty acid to an amino acid to form an acyl amino acid. In certain embodiments, a beta-hydroxy fatty acid linkage domain is covalently linked to a peptide synthetase domain and a thioesterase domain to generate an engineered polypeptide useful in the synthesis of an acyl amino acid. In certain embodiments, a beta-hydroxy fatty acid linkage domain is covalently linked to a peptide synthetase domain and a reductase domain to generate an engineered polypeptide useful in the synthesis of an acyl amino acid. A variety of beta-hydroxy fatty acid linkage domains are known to those skilled in the art. However, different beta-hydroxy fatty acid linkage domains often exhibit specificity for one or more beta-hydroxy fatty acids. As one non-limiting example, the beta-hydroxy fatty acid linkage domain from surfactin synthetase is specific for the beta-hydroxy myristic acid, which contains 13 to 15 carbons in the fatty acid chain. Thus, the beta-hydroxy fatty acid linkage domain from surfactin synthetase can be used in accordance with the present invention to construct an engineered polypeptide useful in the generation of an acyl amino acid that comprises the fatty acid beta-hydroxy myristic acid.

Beta-hydroxy fatty acid: The term "beta-hydroxy fatty acid" as used herein refers to a fatty acid chain comprising a hydroxy group at the beta position of the fatty acid chain. As is understood by those skilled in the art, the beta position corresponds to the third carbon of the fatty acid chain, the first carbon being the carbon of the carboxylate group. Thus, when used in reference to an acyl amino acid of the present invention, where the carboxylate moiety of the fatty acid has been covalently attached to the nitrogen of the amino acid, the beta position corresponds to the carbon two carbons removed from the carbon having the ester group. A beta-hydroxy fatty acid to be used in accordance with the present invention may contain any number of carbon atoms in the fatty acid chain. As non-limiting examples, a beta-hydroxy fatty acid may contain 3, 4, 5, 6, 7, 8, 9, 10, 11, 12, 3, 14, 15, 15, 16, 17, 18, 19, 20 or more carbon atoms. Beta-hydroxy fatty acids to be used in accordance with the present invention may contain linear carbon chains, in which each carbon of the chain, with the exception of the terminal carbon atom and the carbon attached to the nitrogen of the amino acid, is directly covalently linked to two other carbon atoms. Additionally or alternatively, beta-hydroxy fatty acids to be used in accordance with the present invention may contain branched carbon chains, in which at least one carbon of the chain is directly covalently linked to three or more other carbon atoms. Beta-hydroxy fatty acids to be used in accordance with the present invention may contain one or more double bonds between adjacent carbon atoms. Alternatively, beta-hydroxy fatty acids to be used in accordance with the present invention may contain only single-bonds between adjacent carbon atoms. A non-limiting exemplary beta-hydroxy fatty acid that may be used in accordance with the present invention is beta-hydroxy myristic acid, which contains 13 to 15 carbons in the fatty acid chain. Those of ordinary skill in the art will be aware of various beta-hydroxy fatty acids that can be used in accordance with the present invention. Different beta-hydroxy fatty acid linkage domains that exhibit specificity for other beta-hydroxy fatty acids (e.g., naturally or non-naturally occurring beta-hydroxy fatty acids) may be used in accordance with the present invention to generate any acyl amino acid of the practitioner's choosing.

Domain, Polypeptide domain: The terms "domain" and "polypeptide domain" as used herein generally refer to polypeptide moieties that naturally occur in longer polypeptides, or to engineered polypeptide moieties that are homologous to such naturally occurring polypeptide moieties, which polypeptide moieties have a characteristic structure (e.g., primary structure such as the amino acid sequence of the domain, although characteristic structure of a given domain also encompasses secondary, tertiary, quaternary, etc. structures) and exhibit one or more distinct functions. As will be understood by those skilled in the art, in many cases polypeptides are modular and are comprised of one or more polypeptide domains, each domain exhibiting one or more distinct functions that contribute to the overall function of the polypeptide. The structure and function of many such domains are known to those skilled in the art. For example, Fields and Song (Nature, 340 (6230): 245-6, 1989) showed that transcription factors are comprised of at least two polypeptide domains: a DNA binding domain and a transcriptional activation domain, each of which contributes to the overall function of the transcription factor to initiate or enhance transcription of a particular gene that is under control of a particular promoter sequence. A polypeptide domain, as the term is used herein, also refers an engineered polypeptide that is homologous to a naturally occurring polypeptide domain. "Homologous", as the term is used herein, refers to the characteristic of being similar at the nucleotide or amino acid level to a reference nucleotide or polypeptide. For example, a polypeptide domain that has been altered at one or more positions such that the amino acids of the reference polypeptide have been substituted with amino acids exhibiting similar biochemical characteristics (e.g., hydrophobicity, charge, bulkiness) will generally be homologous to the reference polypeptide. Percent identity and similarity at the nucleotide or amino acid level are often useful measures of whether a given nucleotide or polypeptide is homologous to a reference nucleotide or amino acid. Those skilled in the art will understand the concept of homology and will be able to determine whether a given nucleotide or amino acid sequence is homologous to a reference nucleotide or amino acid sequence.

Engineered: The term "engineered" as used herein refers to a non-naturally occurring moiety that has been created by the hand of man. For example, in reference to a polypeptide, an "engineered polypeptide" refers to a polypeptide that has been designed and/or manipulated to comprise a polypeptide that does not exist in nature. In various embodiments, an engineered polypeptide comprises two or more covalently linked polypeptide domains. Typically such domains will be linked via peptide bonds, although the present invention is not limited to engineered polypeptides comprising polypeptide domains linked via peptide bonds, and encompasses other covalent linkages known to those skilled in the art. One or more covalently linked polypeptide domains of engineered polypeptides may be naturally occurring. Thus, in certain embodiments, engineered polypeptides of the present invention comprise two or more covalently linked domains, at least one of which is naturally occurring. In certain embodiments, two or more naturally occurring polypeptide domains are covalently linked to generate an engineered polypeptide. For example, naturally occurring polypeptide domains from two or more different polypeptides may be covalently linked to generate an engineered polypeptide. In certain embodiments, naturally occurring polypeptide domains of an engineered polypeptide are covalently linked in nature, but are covalently linked in the engineered polypeptide in a way that is different from the way the domains are linked nature. For example, two polypeptide domains that naturally occur in the same polypeptide but which are separated by one or more intervening amino acid residues may be directly covalently linked (e.g., by removing the intervening amino acid residues) to generate an engineered polypeptide of the present invention. Additionally or alternatively, two polypeptide domains that naturally occur in the same polypeptide which are directly covalently linked together (e.g., not separated by one or more intervening amino acid residues) may be indirectly covalently linked (e.g., by inserting one or more intervening amino acid residues) to generate an engineered polypeptide of the present invention. In certain embodiments, one or more covalently linked polypeptide domains of an engineered polypeptide may not exist naturally. For example, such polypeptide domains may be engineered themselves.

Fatty acid linkage domain: The term "fatty acid linkage domain" as used herein refers to a polypeptide domain that covalently links a fatty acid to an amino acid to form an acyl amino acid. In certain embodiments, a fatty acid linkage domain is covalently linked to a peptide synthetase domain and a thioesterase domain to generate an engineered polypeptide useful in the synthesis of an acyl amino acid. In certain embodiments, a fatty acid linkage domain is covalently linked to a peptide synthetase domain and a reductase domain to generate an engineered polypeptide useful in the synthesis of an acyl amino acid. A variety of fatty acids are known to those of ordinary skill in the art, as are a variety of fatty acid linkage domains, such as for example, fatty acid linkage domains present in various peptide synthetase complexes that produce lipopeptides. In certain embodiments, a fatty acid linkage domain of the present invention comprises a beta-hydroxy fatty acid linkage domain.

Naturally occurring: The term "naturally occurring", as used herein when referring to an amino acid, refers to one of the standard group of twenty amino acids that are the building blocks of polypeptides of most organisms, including alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In certain embodiments, the term "naturally occurring" also refers to amino acids that are used less frequently and are typically not included in this standard group of twenty but are nevertheless still used by one or more organisms and incorporated into certain polypeptides. For example, the codons UAG and UGA normally encode stop codons in most organisms. However, in some organisms the codons UAG and UGA encode the amino acids selenocysteine and pyrrolysine. Thus, in certain embodiments, selenocysteine and pyrrolysine are naturally occurring amino acids. The term "naturally occurring", as used herein when referring to a polypeptide or polypeptide domain, refers to a polypeptide or polypeptide domain that occurs in one or more organisms. In certain embodiments, engineered polypeptides of the present invention comprise one or more naturally occurring polypeptide domains that naturally exist in different polypeptides. In certain embodiments, engineered polypeptides of the present invention comprise two or more naturally occurring polypeptide domains that are covalently linked (directly or indirectly) in the polypeptide in which they occur, but are linked in the engineered polypeptide in a non-natural manner. As a non-limiting example, two naturally occurring polypeptide domains that are directly covalently linked may be separated in the engineered polypeptide by one or more intervening amino acid residues. Additionally or alternatively, two naturally occurring polypeptide domains that are indirectly covalently linked may be directly covalently linked in the engineered polypeptide, e.g. by removing one or more intervening amino acid residues. Such engineered polypeptides are not naturally occurring, as the term is used herein.

Peptide synthetase complex: The term "peptide synthetase complex" as used herein refers to an enzyme that catalyzes the non-ribosomal production of a variety of peptides. A peptide synthetase complex may comprise a single enzymatic subunit (e.g., a single polypeptide), or may comprise two or more enzymatic subunits (e.g., two or more polypeptides). A peptide synthetase complex typically comprises at least one peptide synthetase domain, and may further comprise one or more additional domains such as for example, a fatty acid linkage domain, a thioesterase domain, a reductase domain, etc. Peptide synthetase domains of a peptide synthetase complex may comprise two or more enzymatic subunits, with two or more peptide synthetase domains present in a given enzymatic subunit. For example the surfactin peptide synthetase complex (also referred to herein simply as "surfactin synthetase complex") comprises three distinct polypeptide enzymatic subunits: the first two subunits comprise three peptide synthetase domains, while the third subunit comprises a single peptide synthetase domain.

Peptide synthetase domain: The term "peptide synthetase domain" as used herein refers to a polypeptide domain that minimally comprises three domains: an adenylation (A) domain, responsible for selectively recognizing and activating a specific amino acid, a thiolation (T) domain, which tethers the activated amino acid to a cofactor via thioester linkage, and condensation (C) domain, which links amino acids joined to successive units of the peptide synthetase by the formation of amide bonds. A peptide synthetase domain typically recognizes and activates a single, specific amino acid, and in the situation where the peptide synthetase domain is not the first domain in the pathway, links the specific amino acid to the growing peptide chain. In certain embodiments, a peptide synthetase domain is covalently linked to a fatty acid linkage domain such as a beta-hydroxy fatty acid linkage domain and a thioesterase domain, which construct may be advantageously used to generate an acyl amino acid. In certain embodiments, a peptide synthetase domain is covalently linked to a fatty acid linkage domain such as a beta-hydroxy fatty acid linkage domain and a reductase domain, which construct may be advantageously used to generate an acyl amino acid. A variety of peptide synthetase domains are known to those skilled in the art, e.g. such as those present in a variety of nonribosomal peptide synthetase complexes. Those skilled in the art will be aware of methods to determine whether a give polypeptide domain is a peptide synthetase domain. Different peptide synthetase domains often exhibit specificity for one or more amino acids. As one non-limiting example, the first peptide synthetase domain from the surfactin synthetase Srf-A subunit is specific for glutamate. Thus, the peptide synthetase domain from surfactin synthetase can be used in accordance with the present invention to construct an engineered polypeptide useful in the generation of an acyl amino acid that comprises the amino acid glutamate. Different peptide synthetase domains that exhibit specificity for other amino acids (e.g., naturally or non-naturally occurring amino acids) may be used in accordance with the present invention to generate any acyl amino acid of the practitioner's choosing.

Polypeptide: The term "polypeptide" as used herein refers to a series of amino acids joined together in peptide linkages, such as polypeptides synthesized by ribosomal machinery in naturally occurring organisms. The term "polypeptide" also refers to a series of amino acids joined together by non-ribosomal machinery, such as by way of non-limiting example, polypeptides synthesized by various peptide synthetases. Such non-ribosomally produced polypeptides exhibit a greater diversity in covalent linkages than polypeptides synthesized by ribosomes (although those skilled in the art will understand that the amino acids of ribosomally-produced polypeptides may also be linked by covalent bonds that are not peptide bonds, such as the linkage of cystines via di-sulfide bonds). For example, surfactin is a lipopeptide synthesized by the surfactin synthetase complex. Surfactin comprises seven amino acids, which are initially joined by peptide bonds, as well as a beta-hydroxy fatty acid covalently linked to the first amino acid, glutamate. However, upon addition the final amino acid (leucine), the polypeptide is released and the thioesterase domain of the SRFC protein catalyzes the release of the product via a nucleophilic attack of the beta-hydroxy of the fatty acid on the carbonyl of the C-terminal Leu of the peptide, cyclizing the molecule via formation of an ester, resulting in the C-terminus carboxyl group of leucine attached via a lactone bond to the b-hydroxyl group of the fatty acid. Polypeptides can be two or more amino acids in length, although most polypeptides produced by ribosomes and peptide synthetases are longer than two amino acids. For example, polypeptides may be 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500 or more amino acids in length.

Reductase Domain: The term "reductase domain" as used herein refers to a polypeptide domain that catalyzes release of an acyl amino acid produced by a peptide synthetase complex from the peptide synthetase complex. In certain embodiments, a reductase domain is covalently linked to a peptide synthetase domain and a fatty acid linkage domain such as a beta-hydroxy fatty acid linkage domain to generate an engineered polypeptide useful in the synthesis of an acyl amino acid. A variety of reductase domains are found in nonribosomal peptide synthetase complexes from a variety of species. A non-limiting example of a reductase domain that may be used in accordance with the present invention includes the reductase domain from linear gramicidin (ATCC8185). However, any reductase domain that releases an acyl amino acid produced by a peptide synthetase complex from the peptide synthetase complex may be used in accordance with the present invention. Reductase domains are characterized by the presence of the consensus sequence: [LIVSPADNK]-x(9)-{P}-x(2)-Y-[PSTAGNCV]-[STAGNQCIVM]-[STAGC]-K-{PC}-[SAGFYR]-[LIVMSTAGD]-x-{K}-[LIVMFYW]-{D}-x-{YR}-[LIVMFYWGAPTHQ]-[GSACQRHM] (SEQ ID NO: 1), where square brackets ("[ ]") indicate amino acids that are typically present at that position, squiggly brackets ("{ }") indicate amino acids that amino acids that are typically not present at that position, and "x" denotes any amino acid or a gap. X(9) for example denotes any amino acids or gaps for nine consecutive positions. Those skilled in the art will be aware of methods to determine whether a give polypeptide domain is a reductase domain.

Thioesterase domain: The term "thioesterase domain" as used herein refers to a polypeptide domain that catalyzes release of an acyl amino acid produced by a peptide synthetase complex from the peptide synthetase complex. In certain embodiments, a thioesterase domain is covalently linked to a peptide synthetase domain and a fatty acid linkage domain such as a beta-hydroxy fatty acid linkage domain to generate an engineered polypeptide useful in the synthesis of an acyl amino acid. A variety of thioesterase domains are found in nonribosomal peptide synthetase complexes from a variety of species. A non-limiting example of a thioesterase domain that may be used in accordance with the present invention includes the thioesterase domain from the *Bacillus subtilis* surfactin synthetase complex, present in Srf-C subunit. However, any thioesterase domain that releases an acyl amino acid produced by a peptide synthetase complex from the peptide synthetase complex may be used in accordance with the present invention. Thioesterase domains are characterized by the presence of the consensus sequence: [LIV]-{KG}-[LIVFY]-[LIVMST]-G-[HYWV]-S-{YAG}-G-[GSTAC] (SEQ ID NO: 2), where square brackets ("[ ]") indicate amino acids that are typically present at that position, and squiggly brackets ("{ }") indicate amino acids that amino acids that are typically not present at that position. Those skilled in the art will be aware of methods to determine whether a give polypeptide domain is a thioesterase domain.

Engineered Polypeptides Useful in the Generation of Acyl Amino Acids

The present invention provides compositions and methods for the generation of acyl amino acids. In certain embodiments, compositions of the present invention comprise engineered polypeptides that are useful in the production of acyl amino acids. In certain embodiments, engineered polypeptides of the present invention comprise a peptide synthetase domain covalently linked to a fatty acid linkage domain and a thioesterase domain. In certain embodiments, engineered polypeptides of the present invention comprise a peptide synthetase domain covalently linked to a beta-hydroxy fatty acid linkage domain and a thioesterase domain. In certain embodiments, engineered polypeptides of the present invention comprise a peptide synthetase domain covalently linked to a fatty acid linkage domain and a reductase domain. In certain embodiments, engineered polypeptides of the present invention comprise a peptide synthetase domain covalently linked to a beta-hydroxy fatty acid linkage domain and a reductase domain.

In certain embodiments, one or more of a peptide synthetase domain, a fatty acid linkage domain (e.g., a beta-hydroxy fatty acid linkage domain), a thioesterase domain and/or a reductase domain present in an engineered polypeptide of the present invention is naturally occurring. Those of ordinary skill in the art will be aware of naturally occurring polypeptides that comprise one or more such domains, which domains can advantageously be used in accordance with the present invention. A non-limiting example of a naturally occurring polypeptide synthetase complex that comprises, for example, multiple peptide synthetase domains, a beta-hydroxy fatty acid linkage domain and a thioesterase domain includes surfactin synthetase. Engineered polypeptides of the present invention may comprise one or more of these domains that are naturally occurring in the surfactin synthetase complex.

In certain embodiments, an engineered polypeptide of the present invention comprises the first peptide synthetase domain of the surfactin synthetase complex that specifies the first amino acid glutamate, which first peptide synthetase domain is covalently linked to the surfactin synthetase beta-hydroxy fatty acid linkage domain and the surfactin synthetase thioesterase domain. In certain embodiments, the other six naturally occurring peptide synthetase domains of the surfactin synthetase complex are not present in an engineered polypeptide of the present invention. As shown by the present inventors, such an engineered polypeptide, when introduced into a bacterial host (e.g. Bacillus subtilis) produces the acyl amino acid cocoyl glutamate.

In certain embodiments, cocoyl glutamate is produced by an engineered polypeptide comprising the first peptide synthetase domain of the surfactin synthetase complex that specifies the first amino acid glutamate, which first peptide synthetase domain is covalently linked to the surfactin synthetase beta-hydroxy fatty acid linkage domain and a reductase domain. In certain embodiments, such a reductase domain is a naturally occurring reductase domain found in a nonribosomal peptide synthetase complex. In certain embodiments, engineered polypeptides of the present invention comprise a reductase domain from the nonribosomal peptide synthetase complex linear gramicidin, such as, without limitation, the nonribosomal peptide synthetase of Bacillus brevis.

Those of ordinary skill in the art will be aware of a variety of naturally occurring polypeptides that comprise a naturally occurring peptide synthetase domain, fatty acid linkage domain, thioesterase domain and/or reductase domain that may advantageously be incorporated into an engineered polypeptide of the present invention. For example, any of a variety of naturally occurring peptide synthetase complexes (see section below entitled "Peptide Synthetase Complexes") may contain one or more of these domains, which domains may be incorporated into an engineered polypeptide of the present invention. Other non-limiting examples of peptide synthetase complexes include surfactin synthetase, fengycin synthetase, arthrofactin synthetase, lichenysin synthetase, syringomycin synthetase, syringopeptin synthetase, saframycin synthetase, gramicidin synthetase, cyclosporin synthetase, tyrocidin synthetase, mycobacillin synthetase, polymyxin synthetase and bacitracin synthetase.

In certain embodiments, one or more such domains present in an engineered polypeptide of the present invention is not naturally occurring, but is itself an engineered domain. For example, an engineered domain present in an engineered polypeptide of the present invention may comprise one or more amino acid insertions, deletions, substitutions or transpositions as compared to a naturally occurring peptide synthetase domain, fatty acid linkage domain (e.g. a beta-hydroxy fatty acid linkage domain), thioesterase domain and/or reductase domain. In certain embodiments, an engineered peptide synthetase domain, fatty acid linkage domain (e.g. a beta-hydroxy fatty acid linkage domain), thioesterase domain and/or reductase domain present in an engineered polypeptide of the present invention comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or more amino acid insertions as compared to a naturally occurring domain. In certain embodiments, an engineered peptide synthetase domain, fatty acid linkage domain (e.g. a beta-hydroxy fatty acid linkage domain), thioesterase domain and/or reductase domain present in an engineered polypeptide of the present invention comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or more amino acid deletions as compared to a naturally occurring domain.

In certain embodiments, an engineered peptide synthetase domain, fatty acid linkage domain (e.g. a beta-hydroxy fatty acid linkage domain), thioesterase domain and/or reductase domain present in an engineered polypeptide of the present invention comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or more amino acid substitutions as compared to a naturally occurring domain. In certain embodiments, such amino acid substitutions result in an engineered domain that comprises an amino acid whose side chain contains a structurally similar side chain as compared to the amino acid in a naturally occurring peptide synthetase domain, fatty acid linkage domain, thioesterase domain and/or reductase domain. For example, amino acids with aliphatic side chains, including glycine, alanine, valine, leucine, and isoleucine, may be substituted for each other; amino acids having aliphatic-hydroxyl side chains, including serine and threonine, may be substituted for each other; amino acids having amide-containing side chains, including asparagine and glutamine, may be substituted for each other; amino acids having aromatic side chains, including phenylalanine, tyrosine, and tryptophan, may be substituted for each other; amino acids having basic side chains, including lysine, arginine, and histidine, may be substituted for each other; and amino acids having sulfur-containing side chains, including cysteine and methionine, may be substituted for each other.

In certain embodiments, amino acid substitutions result in an engineered domain that comprises an amino acid whose side chain exhibits similar chemical properties to an amino acid present in a naturally occurring peptide synthetase domain, fatty acid linkage domain (e.g. a beta-hydroxy fatty acid linkage domain), thioesterase domain and/or reductase domain. For example, in certain embodiments, amino acids that comprise hydrophobic side chains may be substituted for each other. In some embodiments, amino acids may be substituted for each other if their side chains are of similar molecular weight or bulk. For example, an amino acid in an engineered domain may be substituted for an amino acid present in the naturally occurring domain if its side chains exhibits a minimum/maximum molecular weight or takes up a minimum/maximum amount of space.

In certain embodiments, an engineered peptide synthetase domain, fatty acid linkage domain (e.g. a beta-hydroxy fatty acid linkage domain), thioesterase domain and/or reductase domain present in an engineered polypeptide of the present invention exhibits homology to a naturally occurring peptide synthetase domain, fatty acid linkage domain, thioesterase domain and/or reductase domain. In certain embodiments, an engineered domain of the present invention comprises a polypeptide or portion of a polypeptide whose amino acid sequence is 50, 55, 60, 65, 70, 75, 80, 85 or 90 percent identical or similar over a given length of the polypeptide or portion to a naturally occurring domain. In certain embodiments, an engineered domain of the present invention comprises a polypeptide or portion of a polypeptide whose amino acid sequence is 91, 92, 93, 94, 95, 96, 97, 98, or 99 percent identical or similar over a given length of the polypeptide or portion to a naturally occurring domain. The length of the polypeptide or portion over which an engineered domain of the present invention is similar or identical to a naturally occurring domain may be, for example, 5, 6, 7, 8, 9, 10, 15, 20, 25, 30, 35, 40, 45, 50, 60, 70, 80, 90, 100, 200, 300, 400, 500, 600, 700, 800, 900, 1000 or more amino acids.

In certain embodiments, an engineered peptide synthetase domain, fatty acid linkage domain (e.g. a beta-hydroxy fatty acid linkage domain), thioesterase domain and/or reductase domain present in an engineered polypeptide of the present invention comprises an amino acid sequence that conforms to a consensus sequence of a class of engineered peptide synthetase domains, fatty acid linkage domains, thioesterase domains and/or reductase domains. For example, a thioesterase domain may comprise the consensus sequence: [LIV]-{KG}-[LIVFY]-[LIVMSTFG-[HYWV]-S-{YAG}-G-[GSTAC] (SEQ ID NO: 2), and a reductase domain may comprise the consensus sequence: [LIVSPADNK]-x(9)-{P}-x(2)-Y-[PSTAGNCV]-[STAGNQCIVM]-[STAGC]-K-{PC}-[SAGFYR]-[LIVMSTAGD]-x-{K}-[LIVMFYW]-{D}-x-{YR}-[LIVMFYWGAPTHQ]-[GSACQRHM] (SEQ ID NO: 1).

In certain embodiments, an engineered peptide synthetase domain, fatty acid linkage domain (e.g. a beta-hydroxy fatty acid linkage domain), thioesterase domain and/or reductase domain present in an engineered polypeptide of the present invention is both: 1) homologous to a naturally occurring engineered peptide synthetase domain, fatty acid linkage domain, thioesterase domain and/or reductase domain of the present invention, and 2) comprises an amino acid sequence that conforms to a consensus sequence of a class of engineered peptide synthetase domain, fatty acid linkage domain, thioesterase domain and/or reductase domains.

In certain embodiments, engineered polypeptides of the present invention comprise two or more naturally occurring polypeptide domains that are covalently linked (directly or indirectly) in the polypeptide in which they occur, but are linked in the engineered polypeptide in a non-natural manner. As a non-limiting example, two naturally occurring polypeptide domains that are directly covalently linked may be separated in the engineered polypeptide by one or more intervening amino acid residues. Additionally or alternatively, two naturally occurring polypeptide domains that are indirectly covalently linked may be directly covalently linked in the engineered polypeptide, e.g. by removing one or more intervening amino acid residues. As a non-limiting example, engineered polypeptides of the present invention may comprise a peptide synthetase domain and beta-hydroxy fatty acid linkage domain from the SRFA protein, and a thioesterase domain from the SrfC protein, which peptide synthetase domain, beta-hydroxy fatty acid linkage domain and thioesterase domain are covalently linked to each other (e.g. via peptide bonds).

In certain embodiments, two naturally occurring peptide domains that are from different peptide synthetases are covalently joined to generate an engineered polypeptide of the present invention. As a non-limiting example, engineered polypeptides of the present invention may comprise a peptide synthetase domain and beta-hydroxy fatty acid linkage domain from the SRFA protein, and a reductase domain from the gramicidin synthetase complex, which peptide synthetase domain, beta-hydroxy fatty acid linkage domain and reductase domain are covalently linked to each other (e.g. via peptide bonds).

The present invention encompasses engineered polypeptides comprised of these and other peptide synthetase domains, fatty acid linkage domains, thioesterase domains and reductase domains from a variety of peptide synthetase complexes. In certain embodiments, engineered polypeptides of the present invention comprise at least one naturally occurring polypeptide domain and at least one engineered domain.

In certain embodiments, engineered polypeptides of the present invention comprise one or more additional peptide synthetase domains, fatty acid linkage domains, thioesterase domains and/or reductase domains, and still produce an acyl amino acid of interest. For example, the present inventors have shown that an engineered polypeptide comprising a peptide synthetase domain that specifies the amino acid glutamate, a peptide synthetase domain that specifies the amino acid aspartate, a fatty acid linkage domain that specifies beta-hydroxy myristic acid, and a thioesterase domain (see Example 8) produces cocoyl glutamate in excellent yield. In fact, the cocoyl glutamate yield of this engineered polypeptide exceeded the yield of an engineered polypeptide comprising a peptide synthetase domain that specifies the amino acid glutamate, a fatty acid linkage domain that specifies beta-hydroxy myristic acid, and a thioesterase domain (i.e., lacking the second peptide synthetase domain that specifies the amino acid aspartame). Thus, the present invention encompasses the recognition that engineered polypeptides comprising additional peptide synthetase domains, fatty acid linkage domains, thioesterase domains and/or reductase domains beyond those that are minimally required to produce an acyl amino acid of interest may be advantageous in producing such acyl amino acids.

Acyl Amino Acids

Any of a variety of acyl amino acids may be generated by compositions and methods of the present invention. By employing specific peptide synthetase domains, fatty acid linkage domains, thioesterase domains and/or reductase domains in engineered polypeptides, one skilled in the art will be able to generate a specific acyl amino acids following the teachings of the present invention.

In certain embodiments, acyl amino acids generated by compositions and methods of the present invention comprise an amino acid selected from one of the twenty amino acids commonly employed in ribosomal peptide synthesis. Thus, acyl amino acids of the present invention may comprise alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and/or valine. In certain embodiments, acyl amino acids of the present invention comprise amino acids other than these twenty. For example, acyl amino acids of the present invention may comprise amino acids used less commonly during ribosomal polypeptide synthesis such as, without limitation, selenocysteine and/or pyrrolysine. In certain embodiments, acyl amino acids of the present invention comprise amino acids that are not used during ribosomal polypeptide synthesis such as, without limitation, norleucine, beta-alanine and/or ornithine, and/or D-amino acids.

As will be understood by those of ordinary skill in the art after reading this specification, it will typically be the peptide synthetase domain of engineered polypeptides of the present invention that specify the identity of the amino acid of the acyl amino acid. For example, the first peptide synthetase domain of the SRFA protein of the surfactin synthetase complex recognizes and specifies glutamic acid, the first amino acid in surfactin. Thus, in certain embodiments, engineered polypeptides of the present invention comprise the first peptide synthetase domain of the SRFA protein of the surfactin synthetase complex, such that the acyl amino acid produced by the engineered polypeptide comprises glutamic acid. The present invention encompasses the recognition that engineered polypeptides of the present invention may comprise other peptide synthetase domains from the surfactin synthetase complex and/or other peptide synthetase complexes in order to generate other acyl amino acids.

In certain embodiments, engineered polypeptides of the present invention comprise an engineered peptide synthetase domain that is similar to a naturally occurring peptide synthetase domain. For example, such engineered peptide synthetase domains may comprise one or more amino acid insertions, deletions, substitutions, or transpositions as compared to a naturally occurring peptide synthetase domain. Additionally or alternatively, such engineered peptide synthetase domains may exhibit homology to a naturally occurring peptide synthetase domain, as measured by, for example, percent identity or similarity at the amino acid level. Additionally or alternatively, such engineered peptide synthetase domains may comprise one or more amino acid sequences that conform to a consensus sequence characteristic of a given naturally occurring peptide synthetase domain. In certain embodiments, an engineered peptide synthetase domain that is similar to a naturally occurring peptide synthetase domain retains the amino acid specificity of the naturally occurring peptide synthetase domain. For example, the present invention encompasses the recognition that one or more amino acid changes may be made to the first peptide synthetase domain of the SRFA protein of the surfactin synthetase complex, such that the engineered peptide synthetase domain still retains specificity for glutamic acid. As will be recognized by those of ordinary skill in the art after reading this specification, engineered polypeptides containing such an engineered peptide synthetase domain will be useful in the generation of acyl amino acids comprising glutamate, such as, without limitation, cocoyl glutamate.

Such engineered peptide synthetase domains may exhibit one or more advantageous properties as compared to a naturally occurring peptide synthetase domain. For example, engineered polypeptides comprising such engineered peptide synthetase domains may yield an increased amount of the acyl amino acid, may be more stable in a given host cell, may be less toxic to a given host cell, etc. Those of ordinary skill in the art will understand various advantages of engineered peptide synthetase domains of the present invention, and will be able to recognize and optimize such advantages in accordance with the teachings herein.

In certain embodiments, acyl amino acids generated by compositions and methods of the present invention comprise a fatty acid moiety. A fatty acid of acyl amino acids of the present invention may be any of a variety of fatty acids known to those of ordinary skill in the art. For example, acyl amino acids of the present invention may comprise saturated fatty acids such as, without limitation, butryic acid, caproic acid, caprylic acid, capric acid, lauric acid, myristic acid, palmitic acid, stearic arachidic acid, behenic acid, and/or lignoceric acid. In certain embodiments, acyl amino acids of the present invention may comprise unsaturated fatty acids such as, without limitation, myristoleic acid, palmitoleic acid, oliec acid, linoleic acid, alpha-linolenic acid, arachidonic acid, eicosapentaenoic acid, erucic acid, and/or docosahexaenoic acid. Other saturated and unsaturated fatty acids that may be used in accordance with the present invention will be known to those of ordinary skill in the art. In certain embodiments, acyl amino acids produced by compositions and methods of the present invention comprise beta-hydroxy fatty acids as the fatty acid moiety. As is understood by those of ordinary skill in the art, beta-hydroxy fatty acids comprise a hydroxy group attached to the third carbon of the fatty acid chain, the first carbon being the carbon of the carboxylate group.

As will be understood by those of ordinary skill in the art after reading this specification, it will typically be the fatty acid linkage domain of engineered polypeptides of the present invention that specify the identity of the fatty acid of the acyl amino acid. For example, the beta-hydroxy fatty acid linkage domain of the SRFA protein of the surfactin synthetase complex recognizes and specifies beta-hydroxy myristic acid, the fatty acid present in surfactin. Thus, in certain embodiments, engineered polypeptides of the present invention comprise the beta-hydroxy fatty acid linkage domain of the SRFA protein of the surfactin synthetase complex, such that the acyl amino acid produced by the engineered polypeptide comprises beta-hydroxy myristic acid. The present invention encompasses the recognition that engineered polypeptides of the present invention may comprise other beta-hydroxy fatty acid linkage domains from other peptide synthetase complexes in order to generate other acyl amino acids.

In certain embodiments, engineered polypeptides of the present invention comprise an engineered fatty acid linkage domain (e.g. a beta-hydroxy fatty acid linkage domain) that is similar to a naturally occurring fatty acid linkage domain. For example, such engineered fatty acid linkage domains may comprise one or more amino acid insertions, deletions, substitutions, or transpositions as compared to a naturally occurring fatty acid linkage domain. Additionally or alternatively, such engineered fatty acid linkage domains may exhibit homology to a naturally occurring fatty acid linkage domain, as measured by, for example, percent identity or similarity at the amino acid level. Additionally or alternatively, such engineered fatty acid linkage domains may comprise one or more amino acid sequences that conform to a consensus sequence characteristic of a given naturally occurring fatty acid linkage domain. In certain embodiments, an engineered fatty acid linkage domain that is similar to a naturally occurring fatty acid linkage domain retains the fatty acid specificity of the naturally occurring fatty acid linkage domain. For example, the present invention encompasses the recognition that one or more amino acid changes may be made to the beta-hydroxy fatty acid linkage domain of the SRFA protein of the surfactin synthetase complex, such that the engineered beta-hydroxy fatty acid linkage domain still retains specificity for beta-hydroxy myristic acid. As will be recognized by those of ordinary skill in the art after reading this specification, engineered polypeptides containing such an engineered beta-hydroxy fatty acid linkage domain will be useful in the generation of acyl amino acids comprising beta-hydroxy myristic acid, such as, without limitation, cocoyl glutamate.

Engineered fatty acid linkage domains may exhibit one or more advantageous properties as compared to a naturally occurring fatty acid linkage domain. For example, engineered polypeptides comprising such engineered fatty acid linkage domains may yield an increased amount of the acyl amino acid, may be more stable in a given host cell, may be less toxic to a given host cell, etc. Those of ordinary skill in the art will understand various advantages of engineered fatty acid linkage domains of the present invention, and will be able to recognize and optimize such advantages in accordance with the teachings herein.

Thioesterase and reductase domains are known to function in the release of peptides and lipopeptides from the nonribosomal peptide synthetase complexes that produce them. The thioesterase domain is capable of catalyzing release of a lipopeptide product by hydrolysis rather than cyclization. Engineered *Bacillus* strains have been described by de Ferra and coworkers (de Ferra et al., Journal of Biological Chemistry, 272:40, 25304-25309, 1997). In a first strain, the DNA sequence encoding the thioesterase domain was placed downstream of the DNA sequence encoding module 1 of the srfB gene. In a second strain, the sequence encoding the thioesterase domain was placed downstream of the sequence encoding module 5 of the SRFB protein. The first strain generated a linear lipopeptide with four amino acids (Glu, Leu, d-Leu and Val). The second strain produced a lipopeptide with five amino acids (Glu, Leu, d-Leu, Val and Asp). Thus, de Ferra et al. generated linear lipopeptides fusing a thioesterase domain to the end of a particular protein module. However, since prior to the present disclosure, no peptide synthetase complex, naturally occurring or otherwise, was known to produce a peptide or lipopeptide consisting of only a single amino acid, it was previously unknown whether a thioesterase or reductase domain would be capable of releasing a single amino acid, or an amino acid linked to a fatty acid, such as for example a beta-hydroxy fatty acid, from an engineered polypeptide of the present invention. The present invention advances the state of the art by showing for the first time that acyl amino acids produced by engineered polypeptides of the present invention are released from the engineered polypeptides by both thioesterase and reductase domains. Thus, as will be understood by those of ordinary skill in the art upon reading this specification, it will typically be the thioesterase and/or reductase domain of engineered polypeptides of the present invention that catalyze release of the acyl amino acid from the engineered polypeptide. As non-limiting examples, the present inventors have shown that both the thioesterase domain of the SRFC protein of the surfactin synthetase complex and the reductase domain of the linear gramicidin synthetase complex are effective in releasing cocoyl glutamate from engineered polypeptides of the present invention.

In certain embodiments, engineered polypeptides of the present invention comprise an engineered thioesterase or reductase domain that is similar to a naturally occurring thioesterase or reductase domain. For example, such engineered thioesterase or reductase domains may comprise one or more amino acid insertions, deletions, substitutions, or transpositions as compared to a naturally occurring thioesterase or reductase domain. Additionally or alternatively, such engineered thioesterase or reductase domains may exhibit homology to a naturally occurring thioesterase or reductase domain, as measured by, for example, percent identity or similarity at the amino acid level. Additionally or alternatively, such engineered thioesterase or reductase domains may comprise one or more amino acid sequences that conform to a consensus sequence characteristic of a given naturally occurring thioesterase or reductase domain. In certain embodiments, an engineered thioesterase or reductase domain that is similar to a naturally occurring thioesterase or reductase domain retains the ability of the naturally occurring thioesterase or reductase domain to release an acyl amino acid from the engineered polypeptide that produces it.

Engineered thioesterase or reductase domains may exhibit one or more advantageous properties as compared to a naturally occurring thioesterase or reductase domain. For example, engineered polypeptides comprising such engineered thioesterase or reductase domains may yield an increased amount of the acyl amino acid, may be more stable in a given host cell, may be less toxic to a given host cell, etc. Those of ordinary skill in the art will understand various advantages of engineered thioesterase or reductase domains of the present invention, and will be able to recognize and optimize such advantages in accordance with the teachings herein.

In certain embodiments, compositions and methods of the present invention are useful in large-scale production of acyl amino acids. In certain embodiments, acyl amino acids are produced in commercially viable quantities using compositions and methods of the present invention. For example, engineered polypeptides of the present invention may be used to produce acyl amino acids to a level of at least 5, 6, 7, 8, 9, 10, 11, 12, 13, 14, 15, 16, 17, 18, 19, 20, 30, 40, 50, 60, 70, 80, 90, 100, 110, 120, 130, 140, 150, 150, 200, 250, 300, 400, 500, 600, 700, 800, 900, 1000 mg/L or higher. As will be appreciated by those skilled in the art, biological production of acyl amino acids using engineered polypeptides of the present invention achieves certain advantages over other methods of producing acyl amino acids. For example, as compared to chemical production methods, production of acyl amino acids using compositions and methods of the present invention utilizes more readily available and starting materials that are easier to store, reduces the necessity of using harsh and sometimes dangerous chemical reagents in the manufacturing process, reduces the difficulty and efficiency of the synthesis itself by utilizing host cells as bioreactors, and reduces the fiscal and environmental cost of disposing of chemical by-products. Other advantages will be clear to practitioners who utilize compositions and methods of the present invention.

Host Cells

Engineered polypeptides of the present invention may be introduced in any of a variety of host cells for the production of acyl amino acids. As will be understood by those skilled in the art, engineered polypeptides will typically be introduced into a host cell in an expression vector. So long as a host cell is capable of receiving and propagating such an expression vector, and is capable of expressing the engineered polypeptide, such a host cell is encompassed by the present invention. An engineered polypeptide of the present invention may be transiently or stably introduced into a host cell of interest. For example, an engineered polypeptide of the present invention may be stably introduced by integrating the engineered polypeptide into the chromosome of the host cell. Additionally or alternatively, an engineered polypeptide of the present invention may be transiently introduced by introducing a vector comprising the engineered polypeptide into a host cell, which vector is not integrated into the genome of the host cell, but is nevertheless propagated by the host cell.

In certain embodiments, a host cell is a bacterium. Non-limiting examples of bacteria that are useful as host cells of the present invention include bacteria of the genera *Escherichia, Streptococcus, Bacillus*, and a variety of other genera known to those skilled in the art. In certain embodiments, an engineered polypeptide of the present invention is introduced into a host cell of the species *Bacillus subtilis*.

Bacterial host cells of the present invention may be wild type. Alternatively, bacterial host cells of the present invention may comprise one or more genetic changes as compared to wild type species. In certain embodiments, such genetic changes are beneficial to the production of acyl amino acids in the bacterial host. For example, such genetic changes may result in increased yield or purity of the acyl amino acid, and/or may endow the bacterial host cell with various advantages useful in the production of acyl amino acids (e.g., increased viability, ability to utilize alternative energy sources, etc.).

In certain embodiments, the host cell is a plant cell. Those skilled in the art are aware of standard techniques for introducing an engineered polypeptide of the present invention into a plant cell of interest such as, without limitation, gold bombardment and agrobacterium transformation. In certain embodiments, the present invention provides a transgenic plant that comprises an engineered polypeptide that produces an acyl amino acid of interest. Any of a variety of plants species may be made transgenic by introduction of an engineered polypeptide of the present invention, such that the engineered polypeptide is expressed in the plant and produces an acyl amino acid of interest. The engineered polypeptide of transgenic plants of the present invention may be expressed systemically (e.g. in each tissue at all times) or only in localized tissues and/or during certain periods of time. Those skilled in the art will be aware of various promoters, enhancers, etc. that may be employed to control when and where an engineered polypeptide is expressed.

Insects, including insects that are threats to agriculture crops, produce acyl amino acids that are likely to be important or essential for insect physiology. For example, an enzyme related to peptide synthetases produces the product of the Drosophila Ebony genes, which product is important for proper pigmentation of the fly, but is also important for proper function of the nervous system (see e.g., Richardt et al., Ebony, a novel nonribosomal peptide synthetase for beta-alanine conjugation with biogenic amines in Drosophila, J. Biol. Chem., 278(42):41160-6, 2003). Acyl amino acids are also produced by certain Lepidoptera species that are a threat to crops. Thus, compositions and methods of the present invention may be used to produce transgenic plants that produce an acyl amino acid of interest that kills such insects or otherwise disrupts their adverse effects on crops. For example, an engineered polypeptide that produces an acyl amino acid that is toxic to a given insect species may be introduced into a plant such that insects that infest such a plant are killed. Additionally or alternatively, an engineered polypeptide that produces an acyl amino acid that disrupts an essential activity of the insect (e.g., feeding, mating, etc.) may be introduced into a plant such that the commercially adverse effects of insect infestation are minimized or eliminated. In certain embodiments, an acyl amino acid of the present invention that mitigates an insect's adverse effects on a plant is an acyl amino acid that is naturally produced by such an insect. In certain embodiments, an acyl amino acid of the present invention that mitigates an insect's adverse effects on a plant is a structural analog of an acyl amino acid that is naturally produced by such an insect. Compositions and methods of the present invention are extremely powerful in allowing the construction of engineered polypeptides that produce any of a variety of acyl amino acids, which acyl amino acids can be used in controlling or eliminating harmful insect infestation of one or more plant species.

Peptide Synthetase Complexes

Peptide synthetase complexes are multienzymatic complexes found in both prokaryotes and eukaryotes comprising one or more enzymatic subunits that catalyze the non-ribosomal production of a variety of peptides (see, for example, Kleinkauf et al., Annu Rev. Microbiol. 41:259-289, 1987; see also U.S. Pat. No. 5,652,116 and U.S. Pat. No. 5,795,738). Non-ribosomal synthesis is also known as thiotemplate synthesis (see e.g., Kleinkauf et al.). Peptide synthetase complexes typically include one or more peptide synthetase domains that recognize specific amino acids and are responsible for catalyzing addition of the amino acid to the polypeptide chain.

The catalytic steps in the addition of amino acids include: recognition of an amino acid by the peptide synthetase domain, activation of the amino acid (formation of an aminoacyladenylate), binding of the activated amino acid to the enzyme via a thioester bond between the carboxylic group of the amino acid and an SH group of an enzymatic co-factor, which cofactor is itself bound to the enzyme inside each peptide synthetase domain, and formation of the peptide bonds among the amino acids. A peptide synthetase domain comprises subdomains that carry out specific roles in these steps to form the peptide product. One subdomain, the adenylation (A) domain, is responsible for selectively recognizing and activating the amino acid that is to be incorporated by a particular unit of the peptide synthetase. The activated amino acid is joined to the peptide synthetase through the enzymatic action of another subdomain, the thiolation (T) domain, that is generally located adjacent to the A domain. Amino acids joined to successive units of the peptide synthetase are subsequently linked together by the formation of amide bonds catalyzed by another subdomain, the condensation (C) domain.

Peptide synthetase domains that catalyze the addition of D-amino acids also have the ability to catalyze the recemization of L-amino acids to D-amino acids. Peptide synthetase complexes also typically include a conserved thioesterase domain that terminates the growing amino acid chain and releases the product.

The genes that encode peptide synthetase complexes have a modular structure that parallels the functional domain structure of the complexes (see, for example, Cosmina et al., Mol. Microbiol. 8:821, 1993; Kratzxchmar et al., J. Bacteriol. 171: 5422, 1989; Weckermann et al., Nuc. Acids res. 16:11841, 1988; Smith et al., EMBO J. 9:741, 1990; Smith et al., EMBO J. 9:2743, 1990; MacCabe et al., J. Biol. Chem. 266:12646, 1991; Coque et al., Mol. Microbiol. 5:1125, 1991; Diez et al., J. Biol. Chem. 265:16358, 1990).

Hundreds of peptides are known to be produced by peptide synthetase complexes. Such nonribosomally-produced peptides often have non-linear structures, including cyclic structures exemplified by the peptides surfactin, cyclosporin, tyrocidin, and mycobacillin, or branched cyclic structures exemplified by the peptides polymyxin and bacitracin. Moreover, such nonribosomally-produced peptides may contain amino acids not usually present in ribosomally-produced polypeptides such as for example norleucine, beta-alanine and/or ornithine, as well as D-amino acids. Additionally or alternatively, such nonribosomally-produced peptides may comprise one or more non-peptide moieties that are covalently linked to the peptide. As one non-limiting example, surfactin is a cyclic lipopeptide that comprises a beta-hydroxy fatty acid covalently linked to the first glutamate of the lipopeptide. Other non-peptide moieties that are covalently linked to peptides produced by peptide synthetase complexes are known to those skilled in the art, including for example sugars, chlorine or other halogen groups, N-methyl and N-formyl groups, glycosyl groups, acetyl groups, etc.

Typically, each amino acid of the non ribosomally-produced peptide is specified by a distinct peptide synthetase domain. For example, the surfactin synthetase complex which catalyzes the polymerization of the lipopeptide surfactin consists of three enzymatic subunits. The first two subunits each comprise three peptide synthetase domains, whereas the third has only one. These seven peptide synthetase domains are responsible for the recognition, activation, binding and polymerization of L-Glu, L-Leu, D-Leu, L-Val, L-Asp, D-Leu and L-Leu, the amino acids present in surfactin.

A similar organization in discrete, repeated peptide synthetase domains occurs in various peptide synthetase genes in a variety of species, including bacteria and fungi, for example srfA (Cosmina et al., Mol. Microbiol. 8, 821-831, 1993), grsA and grsB (Kratzxchmar et al., J. Bacterial. 171, 5422-5429, 1989) tycA and tycB (Weckermann et al., Nucl. Acid. Res. 16, 11841-11843, 1988) and ACV from various fungal species (Smith et al., EMBO J. 9, 741-747, 1990; Smith et al., EMBO J. 9, 2743-2750, 1990; MacCabe et al., J. Biol. Chem. 266, 12646-12654, 1991; Coque et al., Mol. Microbiol. 5, 1125-1133, 1991; Diez et al., J. Biol. Chem. 265, 16358-16365, 1990). The peptide synthetase domains of even distant species contain sequence regions with high homology, some of which are conserved and specific for all the peptide synthetases. Additionally, certain sequence regions within peptide synthetase domains are even more highly conserved among peptide synthetase domains which recognize the same amino acid (Cosmina et al., Mol. Microbiol. 8, 821-831, 1992).

Surfactin and Surfactin Synthetase

Surfactin is cyclic lipopeptide that is naturally produced by certain bacteria, including the Gram-positive endospore-forming bacteria *Bacillus subtilis*. Surfactin is an amphiphilic molecule (having both hydrophobic and hydrophilic properties) and is thus soluble in both organic solvents and water. Surfactin exhibits exceptional surfactant properties, making it a commercially valuable molecule.

Due to its surfactant properties, surfactin also functions as an antibiotic. For example, surfactin is known to be effective as an anti-bacterial, anti-viral, anti-fungal, anti-mycoplasma and hemolytic compound.

An anti-bacterial compound, surfactin it is capable of penetrating the cell membranes of all types of bacteria, including both Gram-negative and Gram-positive bacteria, which differ in the composition of their membrane. Gram-positive bacteria have a thick peptidoglycan layer on the outside of their phospholipid bilayer. In contrast, Gram-negative bacteria have a thinner peptidoglycan layer on the outside of their phospholipid bilayer, and further contain an additional outer lipopolysaccharide membrane. Surfactin's surfactant activity permits it to create a permeable environment for the lipid bilayer and causes disruption that solubilizes the membrane of both types of bacteria. In order for surfactin to carry out minimal antibacterial effects, the minimum inhibitory concentration (MIC) is in the range of 12-50 µg/ml.

In addition to its antibacterial properties, surfactin also exhibits antiviral properties, and its known to disrupt enveloped viruses such as HIV and HSV. Surfactin not only disrupts the lipid envelope of viruses, but also their capsids through ion channel formations. Surfactin isoforms containing fatty acid chains with 14 or 15 carbon atoms exhibited improved viral inactivation, thought to be due to improved disruption of the viral envelope.

Surfactin consists of a seven amino acid peptide loop, and a hydrophobic fatty acid chain (beta-hydroxy myristic acid) that is thirteen to fifteen carbons long. The fatty acid chain allows permits surfactin to penetrate cellular membranes. The peptide loop comprises the amino acids L-asparagine, L-leucine, glycine, L-leucine, L-valine and two D-leucines. Glycine and asparagine residues at positions 1 and 6 respectively, constitute a minor polar domain. On the opposite side, valine residue at position 4 extends down facing the fatty acid chain, making up a major hydrophobic domain.

Surfactin is synthesized by the surfactin synthetase complex, which comprises the three surfactin synthetase polypeptide subunits SrfA-A, SrfA-B, and SrfA-C. The surfactin synthetase polypeptide subunits SrfA-A and SrfA-B each comprise three peptide synthetase domains, each of which adds a single amino acid to the growing surfactin peptide, while the monomodular surfactin synthetase polypeptide subunit SrfA-C comprises a single peptide synthetase domain and adds the last amino acid residue to the heptapeptide. Additionally the SrfA-C subunit comprises a thioesterase domain, which catalyzes the release of the product via a nucleophilic attack of the beta-hydroxy of the fatty acid on the carbonyl of the C-terminal Leu of the peptide, cyclizing the molecule via formation of an ester.

The spectrum of the beta-hydroxy fatty acids was elucidated as iso, anteiso C13, iso, normal C14 and iso, anteiso C15, and a recent study has indicated that surfactin retains an R configuration at C-beta (Nagai et al., Study on surfactin, a cyclic depsipeptide. 2. Synthesis of surfactin B2 produced by *Bacillus* natto KMD 2311. Chem Pharm Bull (Tokyo) 44: 5-10, 1996).

EXAMPLES

Example 1

Engineering of a FA-GLU-TE Construct Using a Fusion Points Between GLU and TE Upstream of the Consensus Sequence GGHSL (SEQ ID NO: 74)

GGHSL (SEQ ID NO: 74) is a common sequence present in thiolation domains. The strain that was used for the synthesis of FA-Glu is 14311_D3 (OKB105 Δ(upp)Spect$^R$(Δ mod 2)). This strain contains the SRFA, SRFB and SRFC genes necessary to synthesize wild type surfactin, with the exception that the second module of the SRFA gene necessary to catalyze addition the second amino acid (leucine) has been deleted in this strain.

In this example, we started with the plasmid pUC19-UPP-KAN (an engineered pUC 19 plasmid that contains the *B. subtilis* upp gene and the kanamycin resistance gene from *Enterococcus faecalis*) and cloned upstream of upp a ~1 kb DNA fragment that encodes the C-terminus of the SFRA module, which catalyzes the synthesis of the first Glu amino acid of surfactin. Due to the high similarity that exists among surfactin modules, it was advantageous to do nested PCR reactions to amplify genomic DNA sequences. The C-terminus of the module that specifies Glu was obtained from the genomic DNA of strain OKB105 using primers 026663:5'-ATGATTACAGCTATCATGGGAATTTTAA-3' [SEQ ID NO: 3] and 026670:5'-GCGGTGAAGAAACAG-GATACGTA-3' [SEQ ID NO: 4].

The resulting PCR product was used as a template for primers: 026682:5'-GCAGATTGTACTGAGAGTGCAC-CATAmUACGCTCGGAACCTTGCCTACA-3' [SEQ ID NO: 5] and 026690:5'-CTGTGCGGTATTTCACACCGm-CGTCAAAGATCCCCGCCTTCTC-3' [SEQ ID NO: 6].

This fragment was annealed to the PCR product obtained from the template pUC19-UPP-KAN and primers: 026688: 5'-GCGGTGTGAAATACCGCACAmGATGCG-TAAGGAGAAAATACC-3' [SEQ ID NO: 7] and 026680:5'-ATATGGTGCACTCTCAGTACAATCTGmCTCTGATG CCGCATAGTTAA-3' [SEQ ID NO: 8].

The product of this annealing reaction was named pUC19-GLU-UPP-KAN. The TE fragment of surfactin was amplified with primers: 026664:5'-ACGACGAACGGGAAAGT-CAAT-3' [SEQ ID NO: 9] and 026671:5'-ATTGTTCAAGAGCCCGGTAATCT-3' [SEQ ID NO: 10].

The PCR product of this reaction was used as a template for primers: 026683:5'-ACATCCGCAACTGTCCATACTCT-mGGATTTCTTTGCGCTCGGAGGGCA-3' [SEQ ID NO: 11] and 026691:5'-AGCTATGACCATGATTACGC-CAAmGTGATAACCGCCTGCGGAAAGA-3' [SEQ ID NO: 12]

This fragment was annealed to the PCR product obtained from pUC19-GLU-UPP-KAN opened with primers: 026689: 5'-CTTGGCGTAATCATGGTCATAGC-mUGTTTCCTGTGTGAAATTGTTAT-3' [SEQ ID NO: 13] and 026681:5'-CAGAGTATGGACAGTTGCGGATG-mUACTTCAGAAAAGATTAGATGTCTAA-3' 3' [SEQ ID NO: 14].

The product of this annealing reaction was named pUC19-GLU-UPP-KAN-TE. This plasmid was used to transform 013627 (OKB105 Δ(upp)SpectR(Δ mod 2)). The resulting strain was named OKB105 Δ(upp)SpectR(Δ mod(2-7)) upp+ KanR. A seamless construct was obtained by using pUC19-KAN, which was obtained from pUC19-UPP-KAN by using primers: Del-UPP and AMP-FW:5'-ATATCTCTAGAA-CACTATCAmCGATAAACCCAGCGAAC-CATTTGAGGTG-3' [SEQ ID NO: 15] and Del-UPP-BK:5'-GTGATAGTGTTCTAGAGATAmUGGTGCACTCTCAG TACAATCTGCTCTG-3'[SEQ ID NO: 16]. The PCR product was self-annealed and transformed into Sure cells. The resulting plasmid was named pUC19-KAN.

The plasmid pUC19-KAN was used as a template to engineer a variant of this plasmid to introduce a seamless deletion of modules 2-7 and removed the upp-kan marker introduced into strain OKB105 Δ(upp)Spect$^R$(Δ mod(2-7)) upp$^+$Kan$^R$. The first step in the creation of that plasmid was the introduction of the TE domain of surfactin downstream of the KAN gene of pUC19-KAN. The TE fragment of surfactin was amplified with primers:

```
026664:
5'-ACGACGAACGGGAAAGTCAAT-3'      [SEQ ID NO: 17]
and

026671:
5'-ATTGTTCAAGAGCCCGGTAATCT-3'.   [SEQ ID NO: 18]
```

The PCR product of this reaction was used as a template for primers: 026683:5'-ACATCCGCAACTGTCCATACTCT-mGGATTTCTTTGCGCTCGGAGGGCA-3' [SEQ ID NO: 19] and 026691:5'-AGCTATGACCATGATTACGC-CAAmGTGATAACCGCCTGCGGAAAGA-3' [SEQ ID NO: 20].

This fragment was annealed to the PCR product obtained from pUC19-KAN opened with primers: 026666:5'-CT-GTTTGACAATTCTGTGAAmCTTCCGCTTCCTCGCT-3' [SEQ ID NO: 21] and 026673:5'-CAGAGTATGGACAGT-TGCGGAmUGTACTTCAGAAAAGATTAGATGTCT-3' [SEQ ID NO: 22].

The annealing reaction was transformed into Sure cells and the resulting plasmid was named pUC19-KAN-TE. This plasmid has two DNA sequences that are able to recombine with homologous sequences in OKB105 Δ(upp)Spect$^R$(Δ mod(2-7)) upp$^+$Kan$^R$. However, to make a seamless fusion between the first module of surfactin and the TE, we constructed a modified version of this plasmid containing a short DNA sequence that is homologous to the 3'-end of the Glu sequence, and placed it in between KAN and TE in pUC19-KAN-TE.

The short DNA sequence was obtained using the overlap in sequence that exists among four primers: 026658:5'-ACTCT-GCTGTCAGCGGCACTGCCTATACAGCGC-CGCGAAATGAG-3' [SEQ ID NO: 23], 026659:5'-AAATG-GCTGCGATTGCTTTTTCAGTCTCATTTCGCGGCGCT GTATAGGCAG-3' [SEQ ID NO: 24], 026660:5'-ACT-GAAAAAGCAATCGCAGCCATTTGGCAG-GACGTGCTGAACGTTGAGAAG-3' [SEQ ID NO: 25], and 026661:5'-ATCGTCAAAGATCCCCGCCTTCT-CAACGTTCAGCACGTCCTGCC-3' [SEQ ID NO: 26].

The resulting PCR product was amplified using primers: 026669:5'-ACTCTGCTGTCAGCGGCmACTGCCTATA-CAGCGCCGCGAAAT-3' [SEQ ID NO: 27] and 026676:5'-ATCGTCAAAGATCCCCGmCCTTCT-CAACGTTCAGCACGTCCT-3' [SEQ ID NO: 28] and annealed into the PCR product that resulting from opening pUC19-KAN-TE with primers: 026657:5'-TGCCGCTGA-CAGCAGAGmUATGGACAGTTGCGGATGTACTTCA-3' [SEQ ID NO: 29] and 026662:5'-GCGGGGATCTTTGAC-GAmUTTCTTTGCGCTCGGAGGG-3' [SEQ ID NO: 30].

The annealing reaction was transformed into Sure cells and the resulting plasmid was named pUC19-KAN-DR-TE. This plasmid was transformed into OKB105 Δ(upp)Spect$^R$(Δ mod (2-7)) upp$^+$ Kan$^R$ and the resulting strain was named OKB105 Δ(upp)Spect$^R$ FA-GLU-TE-MG. A description of the process is described in FIG. 1.

Example 2

A Second Strategy for Engineering a FA-GLU-TE Construct Using a Fusion Points Between GLU and TE Upstream of the Consensus Sequence GGHSL (SEQ ID NO: 74)

In this example, we followed a similar strategy to that employed in Example 1 but instead of directly deleting surfactin modules 3-7 in one step, we created an intermediate *Bacillus* strain (OKB105 Δ(upp)Spect$^R$(Δ mod(2-4))) in which we deleted modules 2, 3, and 4 in the surfactin synthetases, and then transformed that strain using pUC19-KAN-DR-TE, as described in Example 1 above, to obtain OKB105 Δ(upp)Spect$^R$ FA-GLU-TE.

The strain used for the engineering of (OKB105 Δ(upp) Spect$^R$(Δ mod(2-4))) was strain 013627 (OKB105 Δ(upp) Spect$^R$(Δ mod 2)). The starting plasmid to mark the chromosome of 013627 was pUC19-GLU-UPP-KAN. Due to the high similarity that exists among modules, it was necessary to do nested PCR reactions to amplify genomic DNA sequences. The C-terminus of the module that encodes Asp was obtained from the genomic DNA of strain OKB105 using primers 026665:5'-TACGTCGGATCAAGATAT-TGAAAAAG-3' [SEQ ID NO: 31] and 026672:5'-ACA-GATCTGTCGCATATTCGAGC-3' [SEQ ID NO: 32].

The resulting PCR product was used as a template for primers: 026684:5'-ACATCCGCAACTGTCCATACTCT-mGCGGAGACAGCGCTTGAAGAAA-3' [SEQ ID NO: 33] and 026692:5'-AGCTATGACCATGATTACGC-CAAmGTACTCCTGATGCTCAAGGGCTG-3' [SEQ ID NO: 34].

This fragment was annealed to the PCR product obtained from pUC19-GLU-UPP-KAN opened with primers: 026689: 5'-CTTGGCGTAATCATGGTCATAGC-mUGTTTCCTGTGTGAAATTGTTAT-3' [SEQ ID NO: 35] and 026681:5'-CAGAGTATGGACAGTTGCGGATG-mUACTTCAGAAAAGATTAGATGTCTAA-3' [SEQ ID NO: 36].

Figure 2:
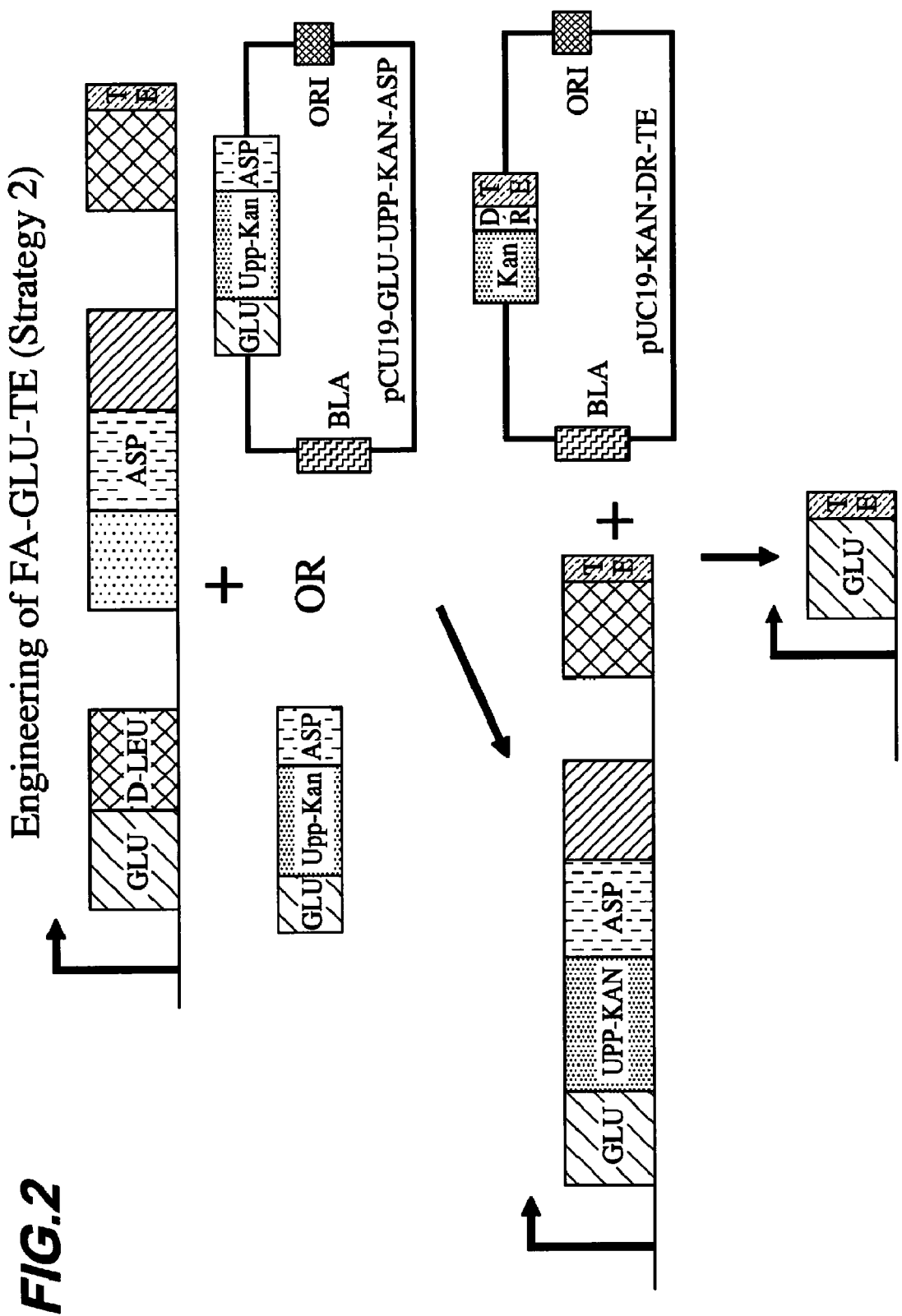
FIG. 2 shows a second embodied strategy for engineering a FA-GLU-TE construct.

The product of this annealing reaction was named pUC19-GLU-UPP-KAN-ASP and was used to transform 013627 (OKB105 Δ(upp)Spect$^R$. Δ(mod 2)). The resulting strain was named OKB105 Δ(upp)Spect$^R$. Δ(mod(2-4)) upp$^+$ Kan$^R$. This strain was then transformed with pUC19-KAN-DR-TE to produce strain OKB105 Δ(upp)Spect$^R$ FA-GLU-TE-MG. The steps used to construct the strain are shown in FIG. 2.

Both strategies described in Examples 1 and 2 produced the desired construct. One strain derived from strategy employed in Example 1, which had the correct sequence to produce FA-GLU, was named 23960_A1 (FA-GLU-TE-MG) and was used in subsequent examples.

Example 3

Engineering a FA-GLU-TE-MH Construct Using Fusion Points Between GLU and TE Downstream of the Consensus Sequence GGHSL (SEQ ID NO: 74)

In addition to the construct described above, where we engineered a fusion between the modules encoding glutamic acid and surfactin's thioesterase domain upstream of the consensus sequence GGHSL (SEQ ID NO: 74), we engineered two additional constructs in which the fusion point was engineered downstream of the consensus sequence GGHSL (SEQ ID NO: 74).

One of these constructs, which we labeled FA-GLU-TE-MH, was engineered by transforming a plasmid, with a modified fusion boundary between GLU and TE, into strain OKB105 Δ(upp)Spect$^R$(Δ mod(2-7)) upp$^+$Kan$^R$. The first step of this strategy was to modify the plasmid pUC19-GLU-UPP-KAN-TE and add the DNA missing to make the fusion between GLU and TE downstream of the consensus sequence GGHSL (SEQ ID NO: 74). Accordingly, the eight primers below, which are partially contiguous, were used as in a PCR as primers and template:

019114:
[SEQ ID NO: 37]
5'-GGGGATCTTTGACAATTTCTTTGAAACTGGCGGACATTCATTA
AA-3';

019115:
[SEQ ID NO: 38]
5'-AATCTTTGTTAAAAGGGTCATGGCTTTTAATGAATGTCCGCCA
GTTTCAA-3';

019116:
[SEQ ID NO: 39]
5'-AGCCATGACCCTTTTAACAAAGATTCATAAGGAAACAGGCATT
GAGATTC-3';

019117:
[SEQ ID NO: 40]
5'-GGATGCTCAAACAAAAATTGTTGCGGAATCTCAATGCCTGTTT
CCTTATG-3';

019118:
[SEQ ID NO: 41]
5'-CGCAACAATTTTTGTTTGAGCATCCGACGATTACGGCTCTTGCA
GAGGAA-3';

019119:
[SEQ ID NO: 42]
5'-CCATCAGAGCCATCAGCTTCCTCTGCAAGAGCCGTAATCGT
C-3'.

The resulting mixture was amplified with primers 019149: 5'-GGGGATCTTTGACAATTTCmUT-TGAAACTGGCGGACATTCATTAAAAGC-3' [SEQ ID NO: 43] and 019150:5'-CCATCAGAGCCATCAGmCTTC-CTCTGCAAGAGCCGTAATCGTCGGATG-3' [SEQ ID NO: 44].

The resulting product was annealed to pUC19-GLU-UPP-KAN-TE, described in Example 1, which was opened with the two primers 019113:5'-AGAAATTGTCAAAGATCCC-mCGCCTTCTCAACGTTCAGC-3' [SEQ ID NO: 45] and 019120:5'-GCTGATGGCTCTGATGmGCTTGCAGGAT-GTAACGATAAT-3' [SEQ ID NO: 46] to remove the KAN gene.

The annealed mixture was transformed into Sure cells to produce the plasmid pUC19-GLU-TE-MH. This plasmid was transformed into the *Bacillus* strain OKB105 Δ(upp) Spect$^R$(Δ mod(2-7)) upp$^+$ Kan$^R$. The resulting strain was named OKB105 Δ(upp)Spect$^R$ FA-GLU-TE-MH.

Example 4

Engineering a FA-GLU-TE-GRN Construct Using Fusion Points Between GLU and TE Downstream of the Consensus Sequence GGHSL (SEQ ID NO: 74)

Construction of the second construct, labeled FA-GLU-TE-GRN, in which a fusion point was engineered between the modules encoding glutamic acid and surfactin's thioesterase downstream of the consensus sequence GGHSL (SEQ ID NO: 74), is described below.

The FA-GLU-TE-GRN construct was engineered by using the ete-pUC19-glu-TE-GRN-ladder-1-sense:5'-TTGAGCT-TCCAGTGAAGCTTTTGTTTGAAGCGC-CGACGATCGCCGGCATTTCAG-3' [SEQ ID NO: 47] and ete-pUC19-glu-TE-GRN-ladder-2-anti:5'-CAGAGC-CCCCGTTTTTCAAATACGCTGAAATGC-CGGCGATCGTCGGCGCTT-3' [SEQ ID NO: 48] primers in a PCR reaction as templates and primers. These primers anneal to each other and protruding 3'-ends are filled in by the polymerase. The blunt ended product is the template for the primers below.

The resulting mixture was amplified with primers GRN-ins-sense:5'-TTGAGCTTCCAGTGAAGCTTTTGTTTm-GAAGCGCCGACGATCGCCGGCATTTC-3'[SEQ ID NO: 49] and GRN-ins-anti:5'-CAGAGC-CCCCGTTTTTCAAATACmGCTGAAATGC-CGGCGATCGTCGGCGCTTC-3' [SEQ ID NO: 50].

The resulting product was annealed to pUC19-GLU-UPP-KAN-TE, described in strategy 1, which was opened with primers ete-pUC19-glu-TE-GRN-sense:5'-CG-TATTTGAAAAACGGGGGCTCTmGATG-GCTTGCAGGATGTAACGAT-3' [SEQ ID NO: 51] and ete-pUC19-glu-TE-GRN-anti:5'-

CAAACAAAAGCTTCACTGGAAGCTCAmATGCCTG
TTT CCTTATGAATCTTTGT-3' [SEQ ID NO: 52].

The annealed mixture was transformed into Sure cells to produce the plasmid pUC19-GLU-TE-GRN. This plasmid was transformed into the *Bacillus* strain OKB105 Δ(upp) SpectR(Δ mod(2-7)) upp+KanR. The resulting strain was named OKB105 Δ(upp)SpectR FA-GLU-TE-GRN.

Figure 3:
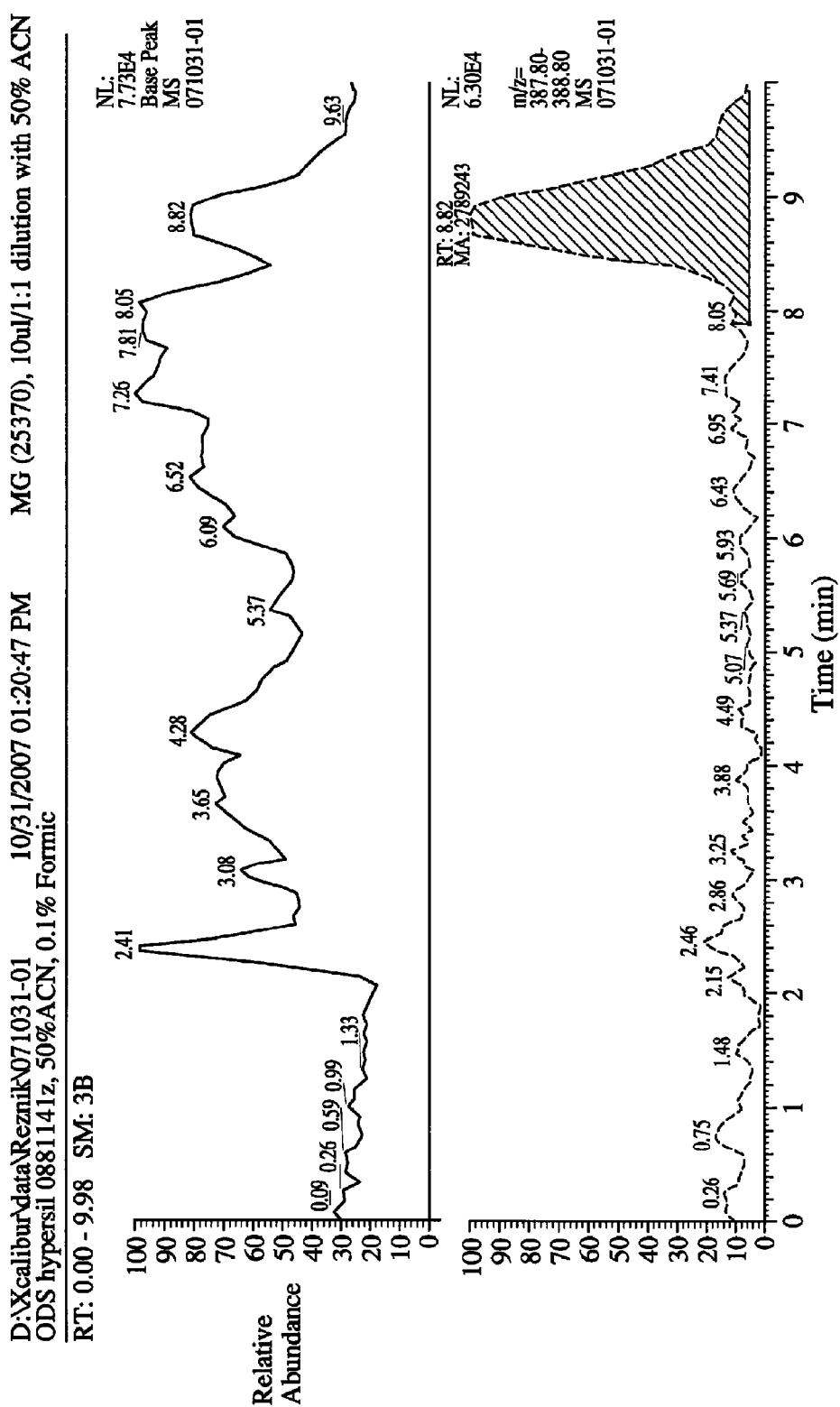
FIG. 3 shows production of FA-GLU by a *Bacillus* strain containing engineered polypeptide GLU-TE-MG.
Figure 4:
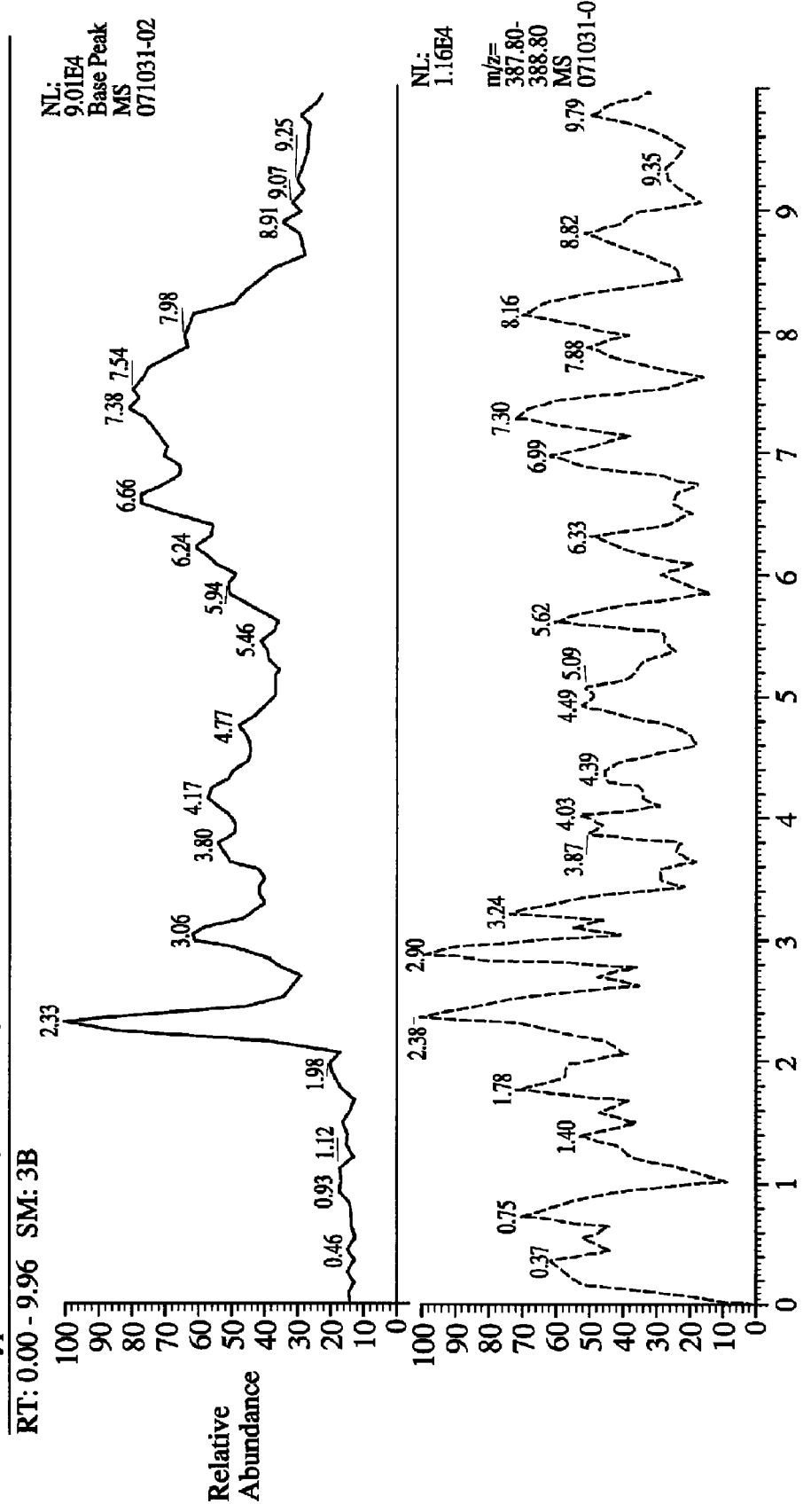
FIG. 4 shows production of FA-GLU by a *Bacillus* strain containing engineered polypeptide GLU-TE-MH.
Figure 5:
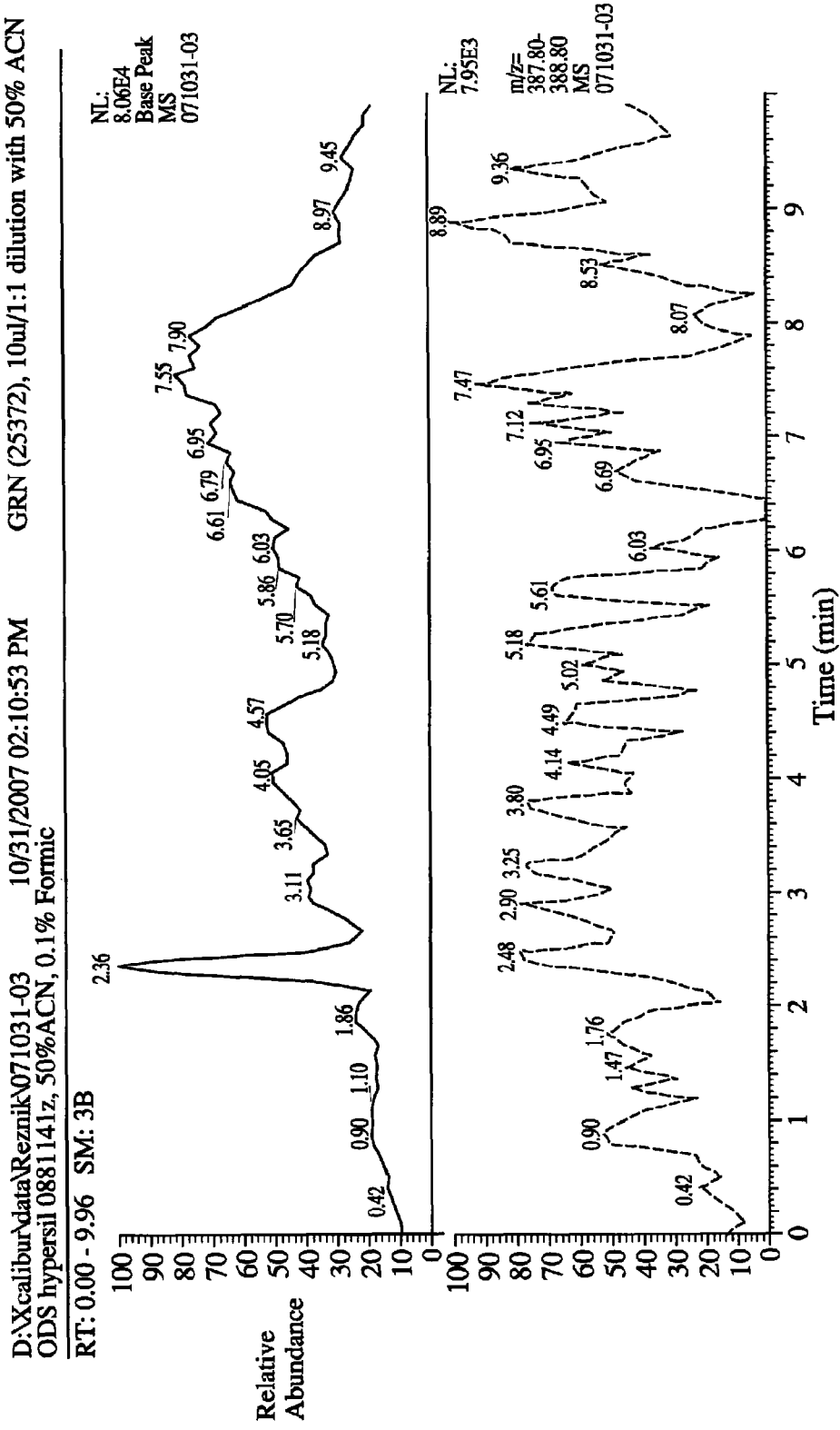
FIG. 5 shows production of FA-GLU by a *Bacillus* strain containing engineered polypeptide FA-GLU-TE-GRN.

Analysis of the production of FA-GLU by strains OKB105 Δ(upp)Spect$^R$ FA-GLU-TE-MG, OKB105 Δ(upp)Spect$^R$ FA-GLU-TE-MH, OKB105 Δ(upp)Spect$^R$ FA-GLU-TE-GRN shows that only the first strain is able to produce detectable amounts of FA-GLU (see FIGS. 3, 4 and 5). Data was obtained using desalted samples by LC-MS quantitation of the area under the peaks with an m/z between 387.8 and 388.8. Strains were grown in M9YE+1% casamino acids and 0.5% glucose for 5 days.

Figure 6:
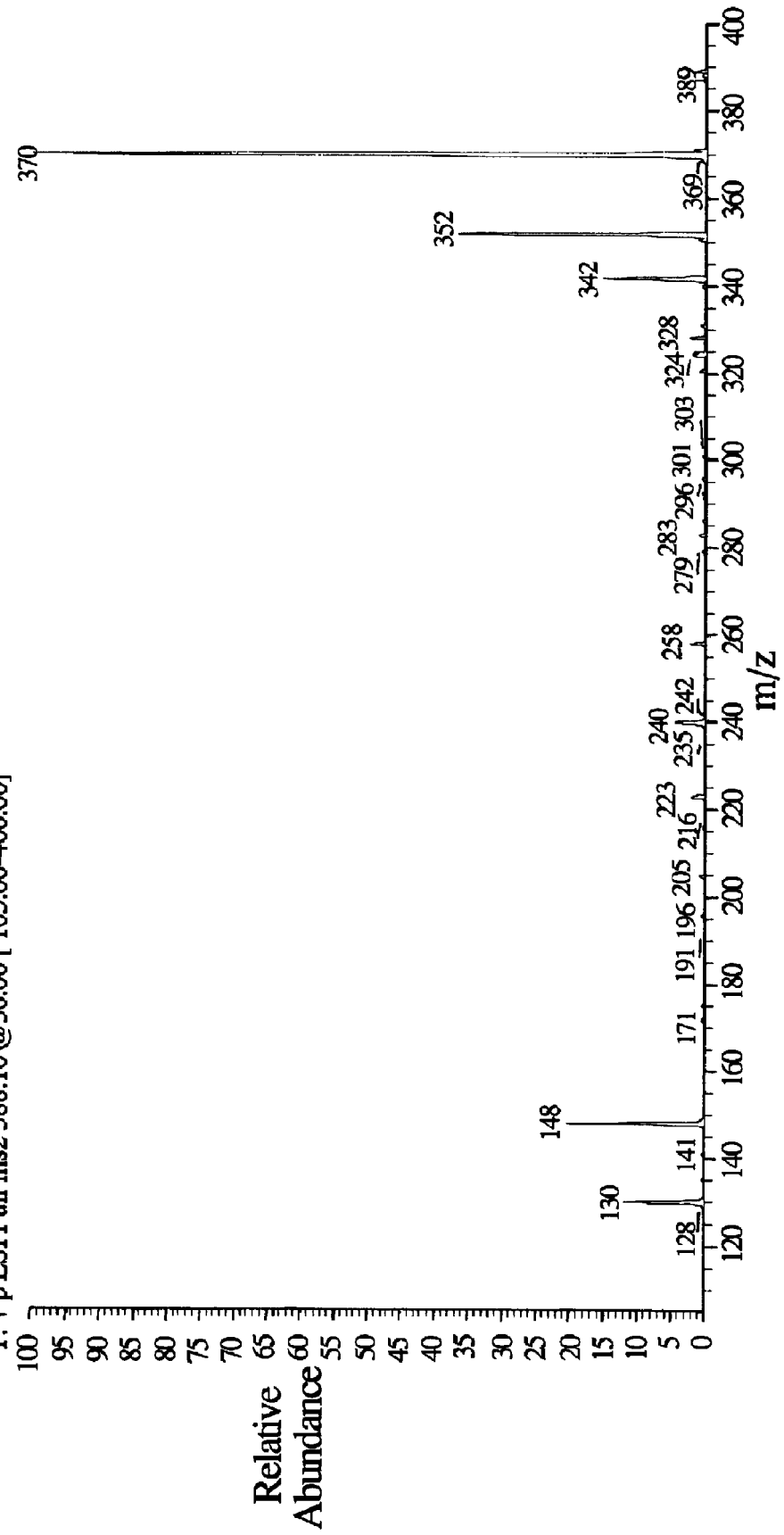
FIG. 6 shows MS-MS analysis of the isolated material derived from OKB105 Δ(upp)Spect$^R$ FA-GLU-TE-MG.

MS-MS analysis of the isolated material derived from OKB105Δ(upp)Spect$^R$ FA-GLU-TE-MG revealed that the isolated product was indeed FA-GLU (see FIG. 6).

Example 5

Analysis of Small Molecule Made by the Strain OKB105Δ(upp)SpectR FA-GLU-TE-MG

In order to characterize the strain under a variety of conditions, OKB105 Δ(upp)SpectR FA-GLU-TE-MG was used to inoculate 1 liter of M9YE containing 1% casamino acids, 0.5% glucose. Twenty-three hours later, after cells had reached saturation, 50 ml aliquots were separately supplemented with various additives, as shown in Table 1 below.

TABLE 1

Supplementation conditions to produce FA-GLU

| Flask | Supplementation |
|---|---|
| 1 | No supplementation |
| 2 | 0.5% Glucose |
| 3 | 0.5% Glycerol |
| 4 | Glutamic Acid 1 mg/ml |
| 5 | Tryptone 10 g/l |
| 6 | Myristic Acid 100 ug/ml |
| 7 | 1% Soy extract |
| 8 | 1% Soy extract + /0.5% Glycerol |

Four days after supplementation, cells and media were treated separately, using the protocols of Folch, and Bligh & Dyer, respectively, to extract fatty acids. The amount recovered from both extractions and each growth conditions are summarized in FIG. 7 and in Table 2 below.

TABLE 2

Total amount of FA-GLU compound recovered

| Growth Conditions used to obtain results | Total titer from liquid and cells |
|---|---|
| Day 0 (0 supplementation) | 9.67 mg/l |
| Day 2 (0 supplementation) | 6.91 mg/l |
| Day 4 (0 supplementation) | 8.16 mg/l |
| Supplemented w/0.5% Glucose | 6.82 mg/l |
| Supplemented w/0.5% Glycerol | 6.70 mg/l |
| Supplemented w/Glut Acid 1 mg/ml | 7.83 mg/l |
| Supplemented w/Tryptone 10 g/l | 7.04 mg/l |
| Supplemented w/Myr Acid 100 ug/ml | 7.22 mg/l |
| Supplemented w/1% Soy extract | 7.28 mg/l |
| Suppl w/1% Soy extract + /0.5% Glycerol | 7.21 mg/l |

Example 6

Engineering a FA-GLU-REDUCTASE Construct

In addition to the constructs in the previous Examples, which make FA-GLU with different fusion points between the module encoding glutamic acid and surfactin's thioesterase (TE) domain, in this example we investigated the effect of replacing surfactin's thioesterase domain with a reductase domain and determined the ability of such a construct to produce FA-GLU.

We amplified the reductase of linear gramicidin (ATCC8185) encoded at the C-terminus of lgrD using primers 019461:5'-CAAGTGCCTGGTTGCGTACAT-3' [SEQ ID NO: 53] and 019462:5'-CGCATTCGATTACTCG-CAAAG-3' [SEQ ID NO: 54]. The resulting PCR product was used as a template for introducing the reductase downstream of the glutamic acid sequence using the fusion points of GLU-TE, GLU-TE-MH, and GLU-TE-GRN.

Example 6A

Engineering a FA-GLU-REDUCTASE-MG Construct

For engineering FA-GLU-REDUCTASE-MG (based on the GLU-TE-MG fusion point), the linear gramicidin reductase PCR template was re-amplified using 019477:5'-TGAGAAGGCGGGGATCTTTGAm-CAATTTCTTTGAGATCGGCGGA-3' [SEQ ID NO: 55] and 019478:5'-CAACGCTTCGACATCACTTTmCT-CAGTTCCGTGTATTTTGTGTCACA-3' [SEQ ID NO: 56] and annealed to PCR product obtained by opening pUC19-GLU-UPP-KAN-TE with 019471:5'-GTCAAAGATC-CCCGCCTTCTCmAACGTTCAGCACGTCCTGCC-3' [SEQ ID NO: 57] and 019472:5'-GAAAGTGATGTC-GAAGCGTTmGATGAATGTCAATCGGGACAATGA-3' [SEQ ID NO: 58].

The annealed mixture was transformed into Sure cells to yield the plasmid pUC19-GLU-RED-TE-MG. This plasmid was transformed into OKB105 Δ(upp)Spect$^R$(Δ mod(2-7)) upp$^+$ Kan$^R$ and the resulting strain was named OKB105 Δ(upp)Spect$^R$ FA-GLU-RED-MG.

Example 6B

Engineering a FA-GLU-REDUCTASE-MH Construct

For engineering FA-GLU-REDUCTASE-MH (based on the GLU-TE-MH fusion point), the linear gramicidin reductase PCR template was re-amplified using 019475:5'-GGCTCTTGCAGAGGAAGCTGAmUGAAAT-TATCAAACACGGTTTGACGT-3' [SEQ ID NO: 59] and 019476:5'-CAACGCTTCGACATCACTTTmCTCAGT-TCCGTGTATTTTGTGTCACA-3' [SEQ ID NO: 60] and annealed to PCR product obtained by opening pUC19-GLU-TE-MH with 019469:5'-ATCAGCTTCCTCTGCAAGAGC-mCGTAATCGTCGGATGCTCAAACAA-3' [SEQ ID NO: 61] and 019470:5'-GAAAGTGATGTCGAAGCGTTmGAT-GAATGTCAATCGGGACAATGA-3' [SEQ ID NO: 62].

The annealed mixture was transformed into Sure cells to yield the plasmid pUC19-GLU-RED-TE-MH. This plasmid was transformed into OKB105 Δ(upp)Spect$^R$(Δ mod(2-7)) upp$^+$ Kan$^R$ and the resulting strain was named OKB105 Δ(upp)Spect$^R$ FA-GLU-RED-MH.

Example 6C

Engineering a FA-GLU-REDUCTASE-GRN Construct

For engineering FA-GLU-REDUCTASE-GRN (based on the GLU-TE-GRN fusion point), the linear gramicidin reductase PCR template was re-amplified using 019473:5'-TCAT-AAGGAAACAGGCATTGAmGGTGCCGT-TGCGCATCTTGTTT-3' [SEQ ID NO: 63] and 019474:5'-CAACGCTTCGACATCACTTTmCTCAGTTCCGTGTAT TTTGTGTCACA-3' [SEQ ID NO: 64] and annealed to PCR product obtained by opening pUC19-GLU-TE-GRN with 019467:5'-CTCAATGCCTGTTTCCTTATG-mAATCTTTGTTAAAAGGGTCATGGCT-3' [SEQ ID NO: 65] and 019468:5'-GAAAGTGATGTCGAAGCGTTmGAT-GAATGTCAATCGGGACAATGA-3' [SEQ ID NO: 66].

The annealed mixture was transformed into Sure cells to yield the plasmid pUC19-GLU-RED-TE-GRN. This plasmid was transformed into OKB105 Δ(upp)Spect$^R$(Δ mod(2-7)) upp$^+$ Kan$^R$ and the resulting strain was named OKB105 Δ(upp)Spect$^R$ FA-GLU-RED-GRN.

Example 7

FA-GLU Production of the Engineered Constructs

The amount of FA-GLU, for each the six constructs in Table 3, was estimated by calculating the area under the curve using LC-MS using sodium cocoyl glutamate as the standard. FIGS. 3, 4, and 5 show the LC-MS data obtained with FA-GLU-TE-MG, FA-GLU-TE-MH, and FA-GLU-TE-GRN, respectively. MALDI data of FA-GLU-TE-MG is shown in FIGS. 8 and 9. Under the best conditions, the amount of FA-GLU obtained with FA-GLU-TE-MG was 9.67 mg/l (see FIG. 7).

TABLE 3

Ability to produce FA-GLU

| Construct | Production of FA-GLU |
| --- | --- |
| FA-GLU-TE-MG | Detected |
| FA-GLU-TE-MH | None detected |
| FA-GLU-TE-GRN | None detected |
| FA-GLU-RED-MG | Detected |
| FA-GLU-RED-MH | Detected |
| FA-GLU-RED-GRN | Detected |

Figure 10:
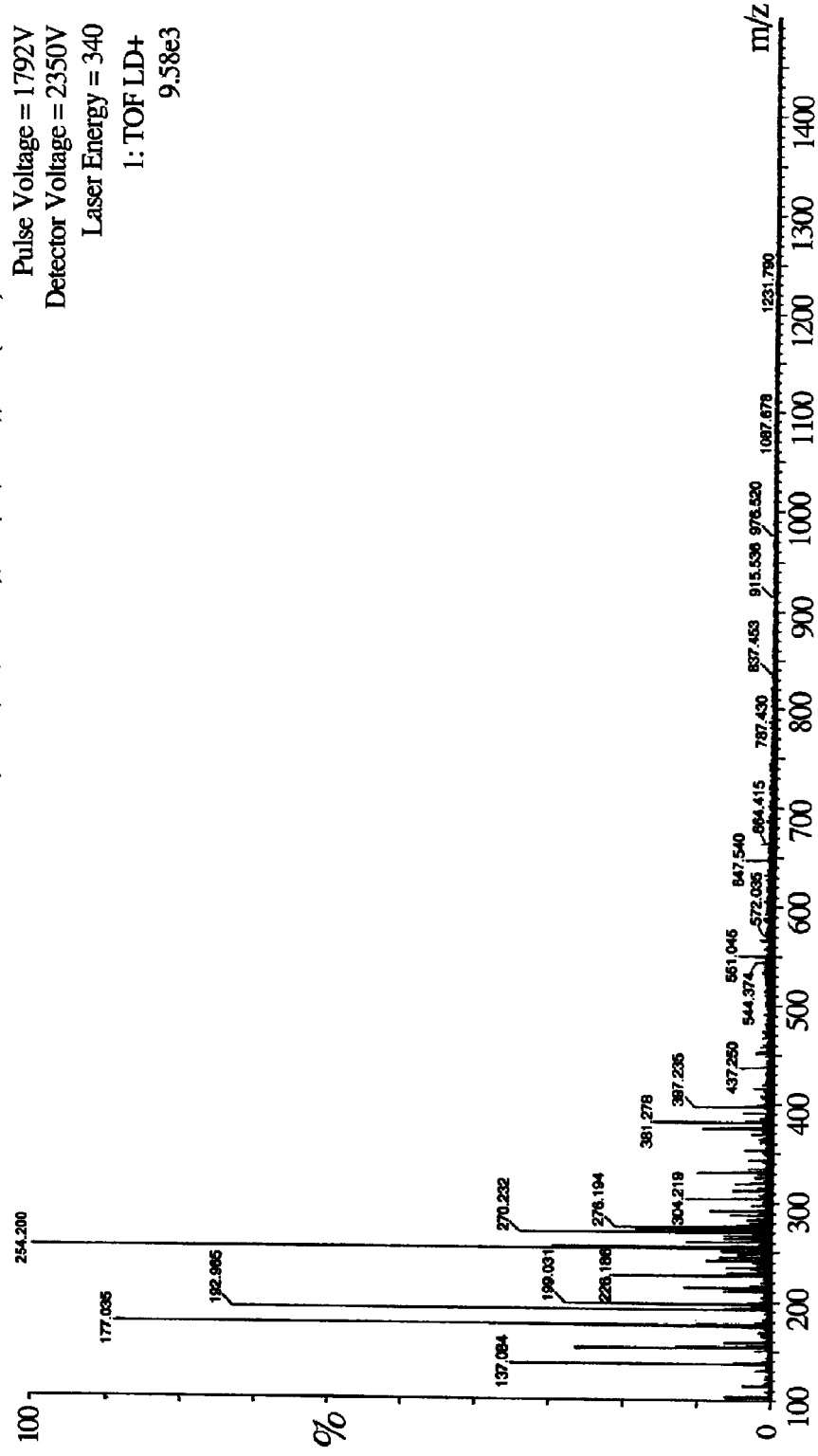
FIG. 10 shows MALDI spectra analysis of FA-GLU-RED-MG.
Figure 11:
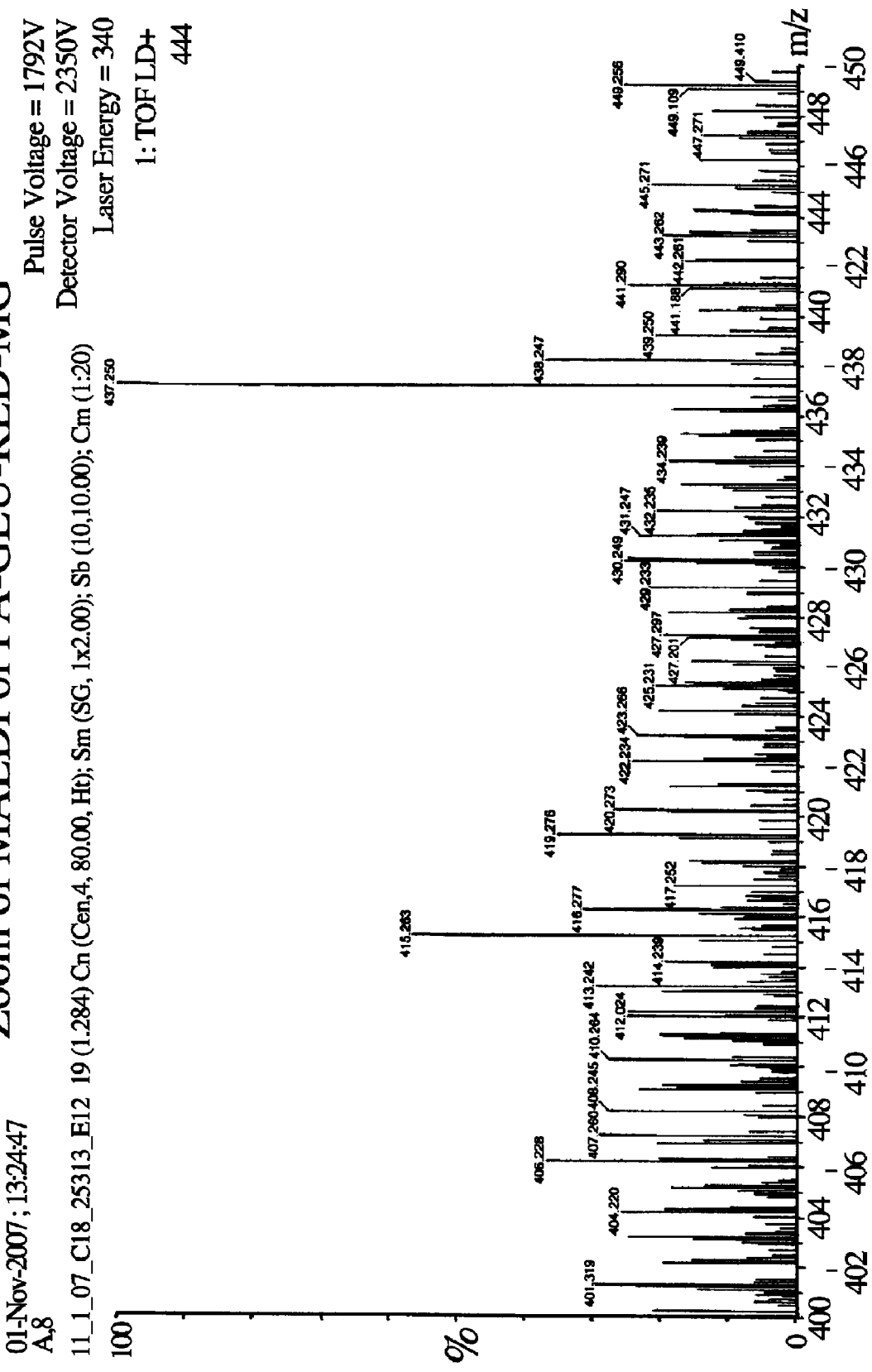
FIG. 11 shows a close up view of the MALDI spectra analysis of FA-GLU-RED-MG shown in FIG. 10.
Figure 12:
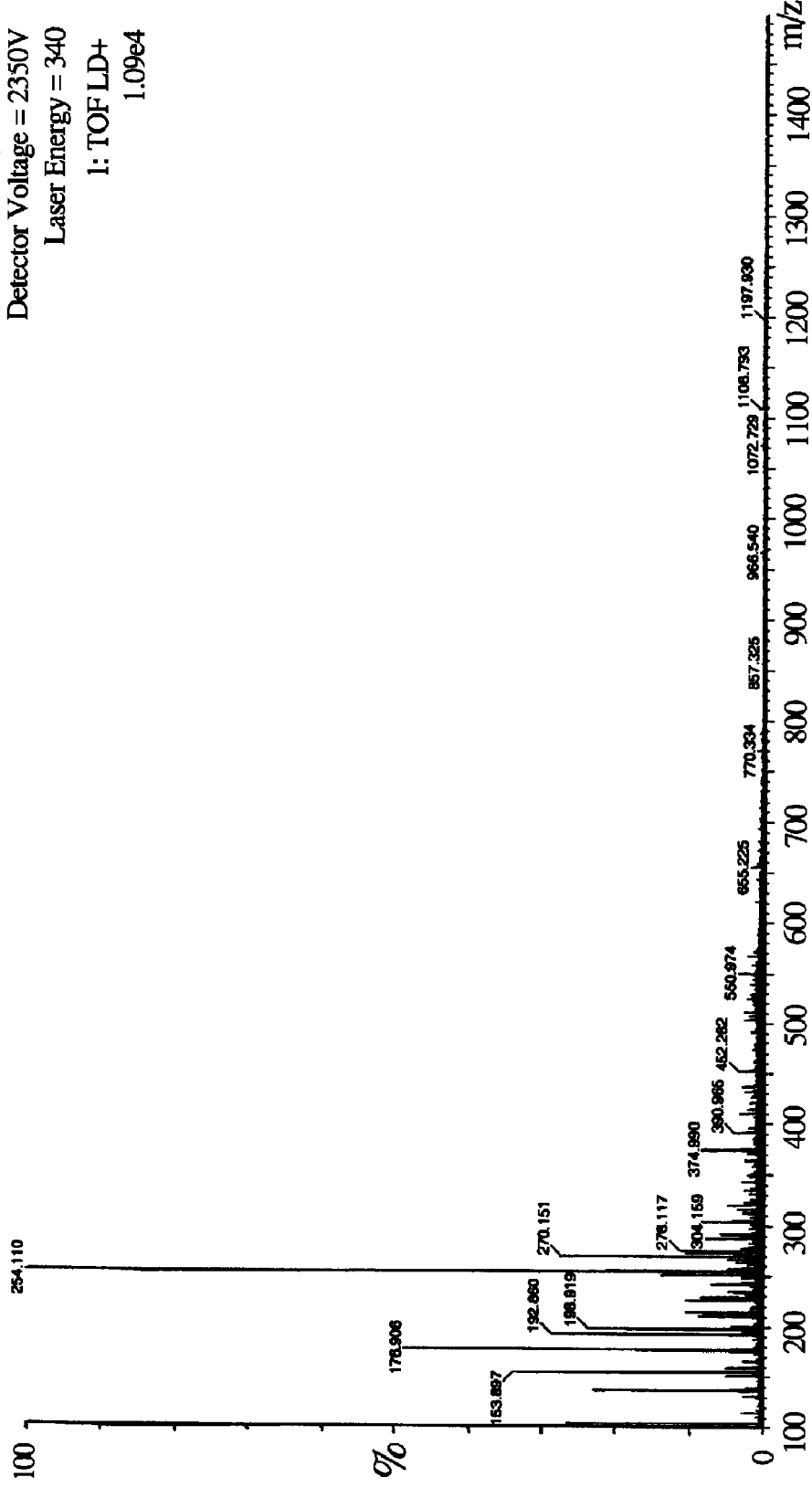
FIG. 12 shows MALDI spectra analysis of FA-GLU-RED-MH.
Figure 13:
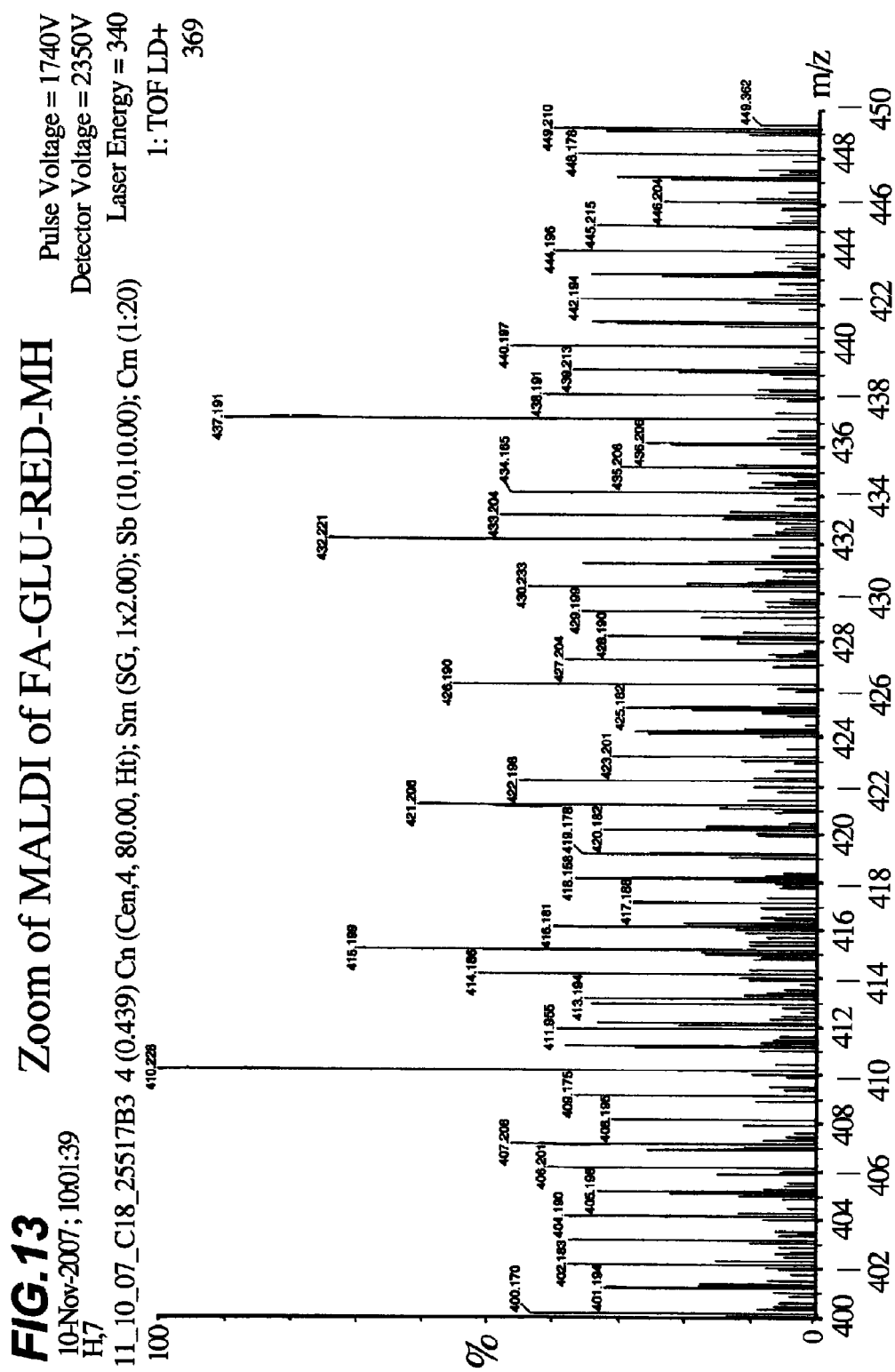
FIG. 13 shows a close up view of the MALDI spectra analysis of FA-GLU-RED-MH shown in FIG. 12.
Figure 14:
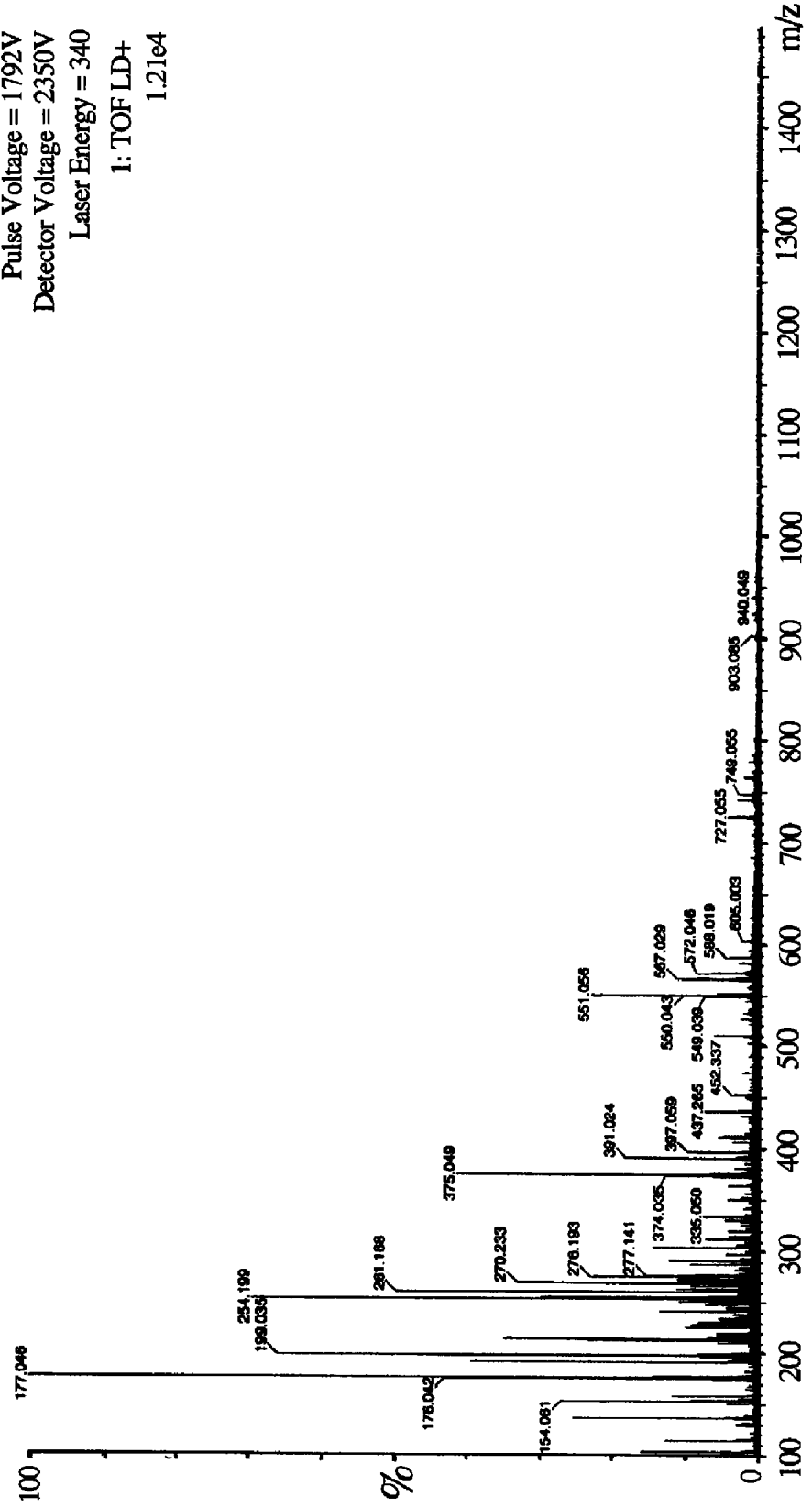
FIG. 14 shows MALDI spectra analysis of FA-GLU-RED-GRN.
Figure 15:
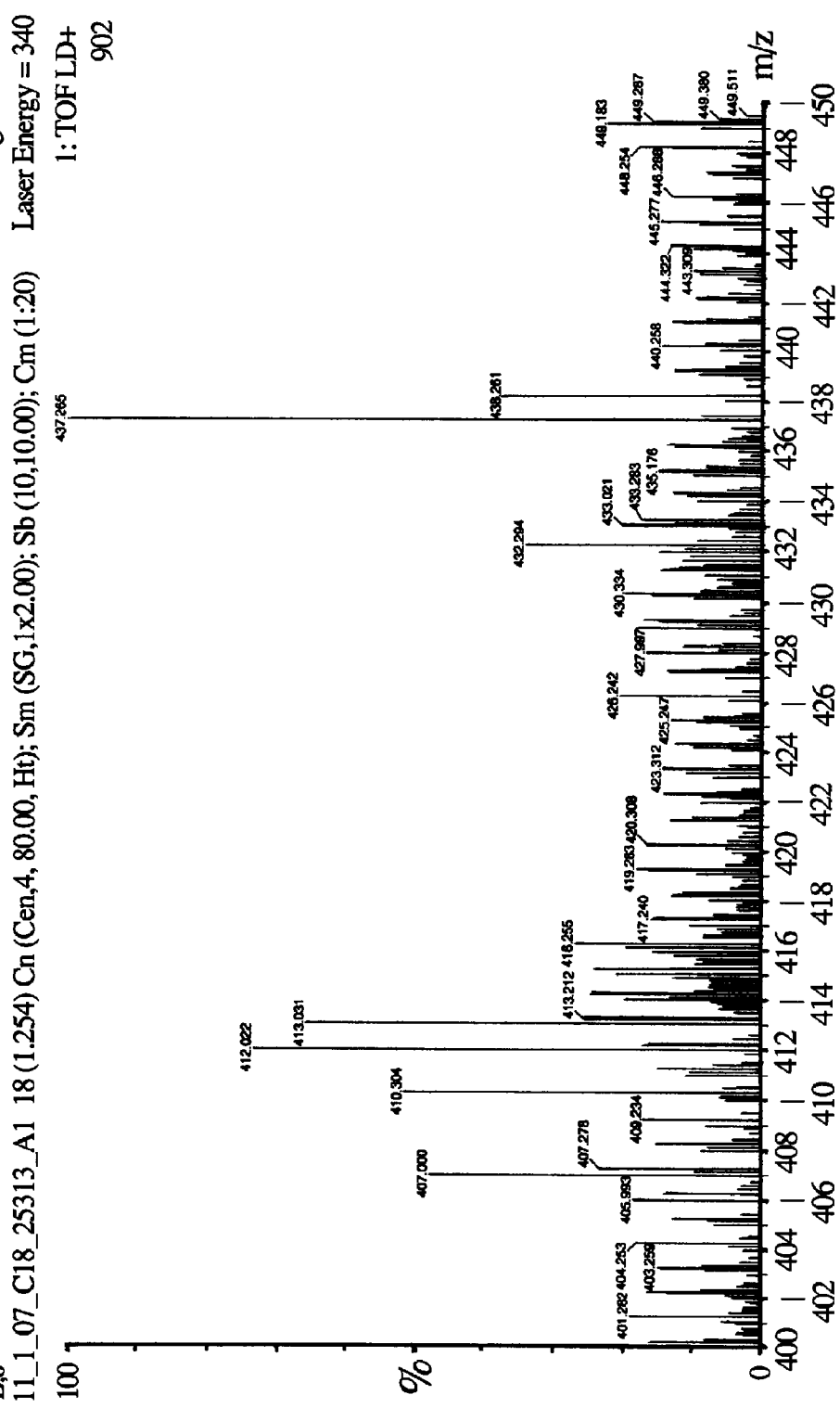
FIG. 15 shows a close up view of the MALDI spectra analysis of FA-GLU-RED-GRN shown in FIG. 14.

When surfactin's thioesterase domain was replaced with linear gramicidin's reductase domain, we were able to detect, by zooming in on the MALDI spectra, data that suggested that FA-GLU-RED-MG (FIGS. 10 and 11), FA-GLU-RED-MH (FIGS. 12 and 13), and FA-GLU-RED-GRN (FIGS. 14 and 15) were able to make FA-GLU. However, analysis by LC-MS showed background levels for all three constructs and no quantitative data was obtained. All quantitative data were obtained from media.

All MALDI data was obtained by passing approximately 0.5 ml of supernatant sample through a C18 column, washed with 10% methanol and eluted with 0.5 ml of 100% methanol. Samples were concentrated 25-fold and then spotted.

Example 8

Engineering of a FA-GLU-ASP-TE-MG Construct

Following up on our most successful construct, we decided to test if we could engineer a construct that would contain a fatty acid followed by glutamic acid covalently linked to aspartic acid using as a fusion point a region located upstream of the consensus sequence GGHSL (SEQ ID NO: 74).

Figure 16:
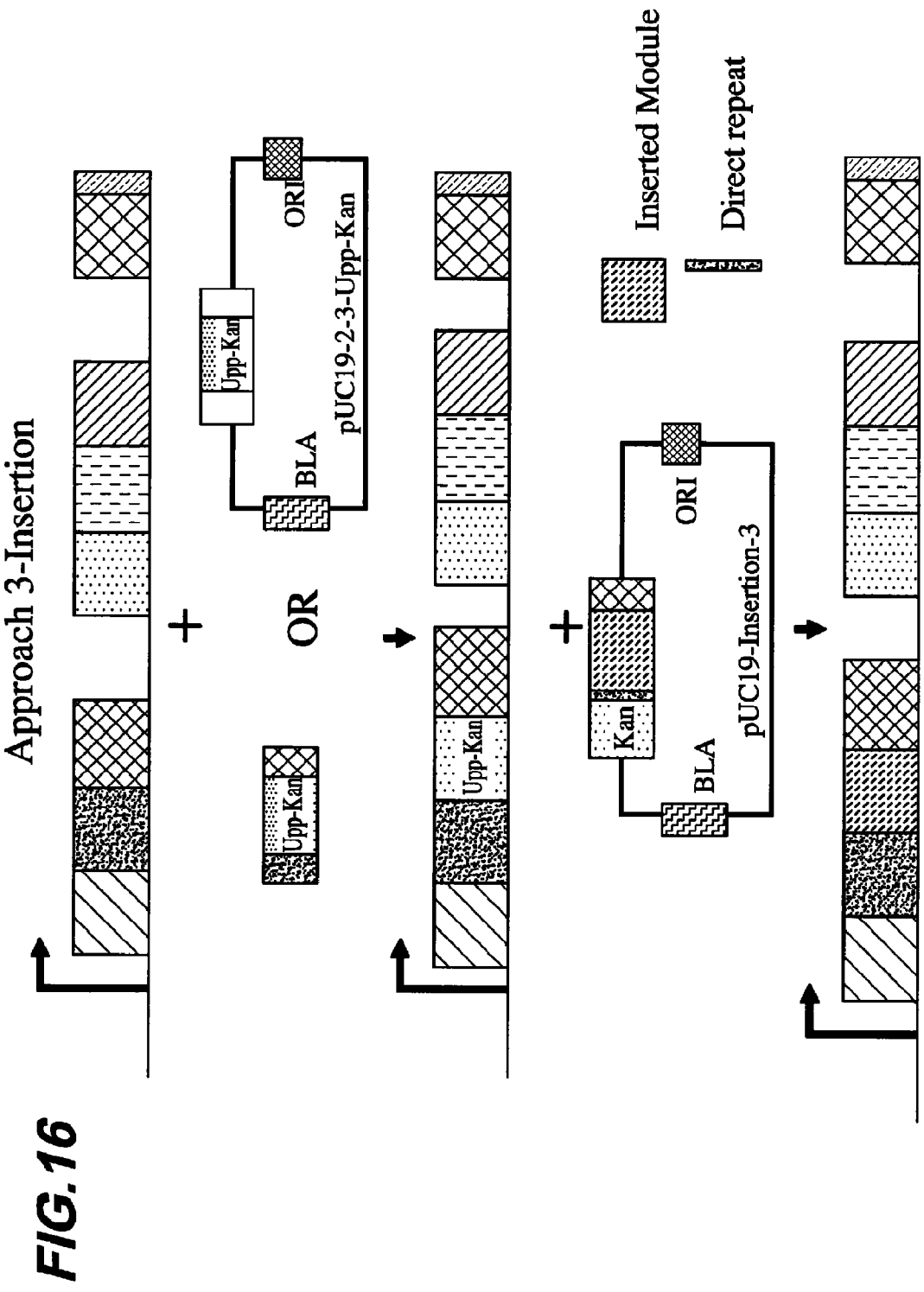
FIG. 16 shows an embodied strategy for engineering a FA-GLU-ASP construct.

The starting strain that was used for the synthesis of FA-GLU-ASP was OKB105 Δ(upp)Spect$^R$(Δ mod(2-7)) upp$^+$ Kan$^R$. The approach that was selected is illustrated in FIG. 16, where the inserted module corresponds to the module that encodes Asp. Due to the high similarity that exists among surfactin modules, it was advantageous to do nested PCR reactions to amplify genomic DNA sequences. The first PCR to amplify a region of DNA encoding ASP was carried out using the outer primers 019129:5'-ACTGAACATGGCT-GAGCATGTG-3' [SEQ ID NO: 67] and 019130:5'-AAGCTCTCCTTCCATTAGAAGAACAG-3' [SEQ ID NO: 68].

Then, the PCR product was further amplified using primers 019133:5'-GAGAAGGCGGGGATCTTTGAmCAACT-TCTTTATGATCGGCGGCC-3' [SEQ ID NO: 69] and 019134:5'-CCTCCGAGCGCAAAGAAATmCGTCAT-CAATGCCGATGGCTTC-3' [SEQ ID NO: 70].

The resulting PCR product was annealed to the PCR product that resulted from amplifying pUC19-KAN-DR-TE with 019131:5'-GTCAAAGATCCCCGCCTTCTmCAACGT-TCAGCACGTCCT-3' [SEQ ID NO: 71] and 019132:5'-GATTTCTTTGCGCTCGGAGmGGCATTC-CTTGAAGGCC-3' [SEQ ID NO: 72] the annealed mixture was transformed into Sure cells. The resulting plasmid was named pUC19-KAN-DR-ASP-TE. A partial sequence of this construct is given in SEQ ID NO: 73, shown below; SEQ ID NO: 73 does not show the 5'-end of the GLU module, which is wild type sequence that corresponds to nucleotide positions 1-1809 of wild type surfactin synthetase. This plasmid was subsequently transformed into OKB105 Δ(upp)Spect$^R$ FA-GLU-ASP-TE-MG.

Cells were grown in M9YE+1% casamino acids and 0.5% glucose for 5 days at 30° C. The supernatant was passed through a C18 column, washed with 10% methanol and eluted with 100% methanol. The eluted material was concentrated and analyzed by MALDI (see FIG. 17). The resulting MS spectra revealed that the expected FA-GLU-ASP-TE was not visible. However, there were four large peaks corresponding to FA-GLU+Na, FA-GLU+K, FA-GLU+2Na, and FA-GLU+Na+K adducts, indicating that the thioesterase had nonspecifically cut the amide bond between the carboxyl group directly linked to the alpha carbon of glutamic acid and the amino group of aspartic acid. LC-MS quantitative analysis revealed that the titer of FA-GLU in the sample derived from the FA-GLU-ASP-TE-MG construct was 116.8 mg/l (see FIG. 18).

TABLE 4

Summary of titer results for the production of FA-GLU

|  | FA-GLU-TE-MG | FA-GLU-ASP-TE-MG |
| --- | --- | --- |
| Highest titer of FA-GLU | 9.67 mg/l | 116.8 mg/l |

The foregoing description is to be understood as being representative only and is not intended to be limiting. Alternative methods and materials for implementing the invention and also additional applications will be apparent to one of skill in the art, and are intended to be included within the accompanying claims.

What is claimed is:

1. A composition comprising an acyl amino acid isolated from a bacterial cell, wherein the acyl amino acid comprises a single natural glutamic acid covalently linked to a natural fatty acid, wherein the natural fatty acid is a beta-hydroxy fatty acid with a branched carbon chain.

2. The composition of claim 1, wherein the natural fatty acid is produced by the bacterial cell and wherein the composition is free of bacterial cell proteins.

3. The composition of claim 1, wherein the natural fatty acid is beta-hydroxy myristic acid.

* * * * *

SEQUENCE LISTING

<160> NUMBER OF SEQ ID NOS: 74

<210> SEQ ID NO 1
<211> LENGTH: 97
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (10)..(18)
<223> OTHER INFORMATION: X is any amino acid or absent
<220> FEATURE:
<221> NAME/KEY: VARIANT
<222> LOCATION: (20)..(21)
<223> OTHER INFORMATION: X is any amino acid or absent
<220> FEATURE:
<221> NAME/KEY: VARIANT
<222> LOCATION: (64)..(64)
<223> OTHER INFORMATION: X is any amino acid or absent
<220> FEATURE:
<221> NAME/KEY: VARIANT
<222> LOCATION: (74)..(74)
<223> OTHER INFORMATION: X is any amino acid or absent

<400> SEQUENCE: 1

Leu Ile Val Ser Pro Ala Asp Asn Lys Xaa Xaa Xaa Xaa Xaa Xaa
1               5                   10                  15

Xaa Xaa Pro Xaa Xaa Tyr Pro Ser Thr Ala Gly Asn Cys Val Ser Thr
                20                  25                  30

Ala Gly Asn Gln Cys Ile Val Met Ser Thr Ala Gly Cys Lys Pro Cys
        35                  40                  45

Ser Ala Gly Phe Tyr Arg Leu Ile Val Met Ser Thr Ala Gly Asp Xaa
    50                  55                  60

Lys Leu Ile Val Met Phe Tyr Trp Asp Xaa Tyr Arg Leu Ile Val Met
65                  70                  75                  80

Phe Tyr Trp Gly Ala Pro Thr His Gln Gly Ser Ala Cys Gln Arg His
                85                  90                  95

Met

<210> SEQ ID NO 2
<211> LENGTH: 31
<212> TYPE: PRT
<213> ORGANISM: Artificial Sequence
<220> FEATURE:
<223> OTHER INFORMATION: Synthetic

<400> SEQUENCE: 2

Leu Ile Val Lys Gly Leu Ile Val Phe Tyr Leu Ile Val Met Ser Thr
1               5                   10                  15

Gly His Tyr Trp Val Ser Tyr Ala Gly Gly Gly Ser Thr Ala Cys
                20                  25                  30

<210> SEQ ID NO 3
<211> LENGTH: 28
<212> TYPE: DNA
<213> ORGANISM: Artificial Sequence
<220> FEATURE:
<223> OTHER INFORMATION: Synthetic

<400> SEQUENCE: 3
atgattacag ctatcatggg aattttaa                                      28

<210> SEQ ID NO 4

```
<211> LENGTH: 23
<212> TYPE: DNA
<213> ORGANISM: Artificial Sequence
<220> FEATURE:
<223> OTHER INFORMATION: Synthetic

<400> SEQUENCE: 4
gcggtgaaga aacaggatac gta                                            23

<210> SEQ ID NO 5
<211> LENGTH: 48
<212> TYPE: DNA
<213> ORGANISM: Artificial Sequence
<220> FEATURE:
<223> OTHER INFORMATION: Synthetic

<400> SEQUENCE: 5
gcagattgta ctgagagtgc accatauacg ctcggaacct tgcctaca                 48

<210> SEQ ID NO 6
<211> LENGTH: 42
<212> TYPE: DNA
<213> ORGANISM: Artificial Sequence
<220> FEATURE:
<223> OTHER INFORMATION: Synthetic

<400> SEQUENCE: 6
ctgtgcggta tttcacaccg cgtcaaagat ccccgccttc tc                       42

<210> SEQ ID NO 7
<211> LENGTH: 41
<212> TYPE: DNA
<213> ORGANISM: Artificial Sequence
<220> FEATURE:
<223> OTHER INFORMATION: Synthetic

<400> SEQUENCE: 7
gcggtgtgaa ataccgcaca gatgcgtaag gagaaaatac c                        41

<210> SEQ ID NO 8
<211> LENGTH: 46
<212> TYPE: DNA
<213> ORGANISM: Artificial Sequence
<220> FEATURE:
<223> OTHER INFORMATION: Synthetic

<400> SEQUENCE: 8
atatggtgca ctctcagtac aatctgctct gatgccgcat agttaa                   46

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
acgacgaacg ggaaagtcaa t                                              21

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
```

```
attgttcaag agcccggtaa tct                                              23

<210> SEQ ID NO 11
<211> LENGTH: 47
<212> TYPE: DNA
<213> ORGANISM: Artificial Sequence
<220> FEATURE:
<223> OTHER INFORMATION: Synthetic

<400> SEQUENCE: 11
acatccgcaa ctgtccatac tctggatttc tttgcgctcg gagggca                    47

<210> SEQ ID NO 12
<211> LENGTH: 45
<212> TYPE: DNA
<213> ORGANISM: Artificial Sequence
<220> FEATURE:
<223> OTHER INFORMATION: Synthetic

<400> SEQUENCE: 12
agctatgacc atgattacgc caagtgataa ccgcctgcgg aaaga                      45

<210> SEQ ID NO 13
<211> LENGTH: 46
<212> TYPE: DNA
<213> ORGANISM: Artificial Sequence
<220> FEATURE:
<223> OTHER INFORMATION: Synthetic

<400> SEQUENCE: 13
cttggcgtaa tcatggtcat agctgtttcc tgtgtgaaat tgttat                     46

<210> SEQ ID NO 14
<211> LENGTH: 49
<212> TYPE: DNA
<213> ORGANISM: Artificial Sequence
<220> FEATURE:
<223> OTHER INFORMATION: Synthetic

<400> SEQUENCE: 14
cagagtatgg acagttgcgg atguacttca gaaaagatta gatgtctaa                  49

<210> SEQ ID NO 15
<211> LENGTH: 48
<212> TYPE: DNA
<213> ORGANISM: Artificial Sequence
<220> FEATURE:
<223> OTHER INFORMATION: Synthetic

<400> SEQUENCE: 15
atatctctag aacactatca cgataaaccc agcgaaccat ttgaggtg                   48

<210> SEQ ID NO 16
<211> LENGTH: 48
<212> TYPE: DNA
<213> ORGANISM: Artificial Sequence
<220> FEATURE:
<223> OTHER INFORMATION: Synthetic

<400> SEQUENCE: 16
gtgatagtgt tctagagata uggtgcactc tcagtacaat ctgctctg                   48

<210> SEQ ID NO 17
<211> LENGTH: 21
<212> TYPE: DNA
<213> ORGANISM: Artificial Sequence
<220> FEATURE:
```

<223> OTHER INFORMATION: Synthetic

<400> SEQUENCE: 17
acgacgaacg ggaaagtcaa t                                              21

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
attgttcaag agcccggtaa tct                                            23

<210> SEQ ID NO 19
<211> LENGTH: 47
<212> TYPE: DNA
<213> ORGANISM: Artificial Sequence
<220> FEATURE:
<223> OTHER INFORMATION: Synthetic

<400> SEQUENCE: 19
acatccgcaa ctgtccatac tctggatttc tttgcgctcg gagggca                  47

<210> SEQ ID NO 20
<211> LENGTH: 45
<212> TYPE: DNA
<213> ORGANISM: Artificial Sequence
<220> FEATURE:
<223> OTHER INFORMATION: Synthetic

<400> SEQUENCE: 20
agctatgacc atgattacgc caagtgataa ccgcctgcgg aaaga                    45

<210> SEQ ID NO 21
<211> LENGTH: 36
<212> TYPE: DNA
<213> ORGANISM: Artificial Sequence
<220> FEATURE:
<223> OTHER INFORMATION: Synthetic

<400> SEQUENCE: 21
ctgtttgaca attctgtgaa cttccgcttc ctcgct                              36

<210> SEQ ID NO 22
<211> LENGTH: 47
<212> TYPE: DNA
<213> ORGANISM: Artificial Sequence
<220> FEATURE:
<223> OTHER INFORMATION: Synthetic

<400> SEQUENCE: 22
cagagtatgg acagttgcgg augtacttca gaaaagatta gatgtct                  47

<210> SEQ ID NO 23
<211> LENGTH: 44
<212> TYPE: DNA
<213> ORGANISM: Artificial Sequence
<220> FEATURE:
<223> OTHER INFORMATION: Synthetic

<400> SEQUENCE: 23
actctgctgt cagcggcact gcctatacag cgccgcgaaa tgag                     44

<210> SEQ ID NO 24

<210> SEQ ID NO 24
<211> LENGTH: 51
<212> TYPE: DNA
<213> ORGANISM: Artificial Sequence
<220> FEATURE:
<223> OTHER INFORMATION: Synthetic

<400> SEQUENCE: 24
aaatggctgc gattgctttt tcagtctcat ttcgcggcgc tgtataggca g    51

<210> SEQ ID NO 25
<211> LENGTH: 51
<212> TYPE: DNA
<213> ORGANISM: Artificial Sequence
<220> FEATURE:
<223> OTHER INFORMATION: Synthetic

<400> SEQUENCE: 25
actgaaaaag caatcgcagc catttggcag gacgtgctga acgttgagaa g    51

<210> SEQ ID NO 26
<211> LENGTH: 44
<212> TYPE: DNA
<213> ORGANISM: Artificial Sequence
<220> FEATURE:
<223> OTHER INFORMATION: Synthetic

<400> SEQUENCE: 26
atcgtcaaag atccccgcct tctcaacgtt cagcacgtcc tgcc    44

<210> SEQ ID NO 27
<211> LENGTH: 41
<212> TYPE: DNA
<213> ORGANISM: Artificial Sequence
<220> FEATURE:
<223> OTHER INFORMATION: Synthetic

<400> SEQUENCE: 27
actctgctgt cagcggcact gcctatacag cgccgcgaaa t    41

<210> SEQ ID NO 28
<211> LENGTH: 41
<212> TYPE: DNA
<213> ORGANISM: Artificial Sequence
<220> FEATURE:
<223> OTHER INFORMATION: Synthetic

<400> SEQUENCE: 28
atcgtcaaag atccccgcct tctcaacgtt cagcacgtcc t    41

<210> SEQ ID NO 29
<211> LENGTH: 42
<212> TYPE: DNA
<213> ORGANISM: Artificial Sequence
<220> FEATURE:
<223> OTHER INFORMATION: Synthetic

<400> SEQUENCE: 29
tgccgctgac agcagaguat ggacagttgc ggatgtactt ca    42

<210> SEQ ID NO 30
<211> LENGTH: 36
<212> TYPE: DNA
<213> ORGANISM: Artificial Sequence
<220> FEATURE:
<223> OTHER INFORMATION: Synthetic

<400> SEQUENCE: 30

```
gcggggatct ttgacgautt ctttgcgctc ggaggg                          36

<210> SEQ ID NO 31
<211> LENGTH: 26
<212> TYPE: DNA
<213> ORGANISM: Artificial Sequence
<220> FEATURE:
<223> OTHER INFORMATION: Synthetic

<400> SEQUENCE: 31
tacgtcggat caagatattg aaaaag                                     26

<210> SEQ ID NO 32
<211> LENGTH: 23
<212> TYPE: DNA
<213> ORGANISM: Artificial Sequence
<220> FEATURE:
<223> OTHER INFORMATION: Synthetic

<400> SEQUENCE: 32
acagatctgt cgcatattcg agc                                        23

<210> SEQ ID NO 33
<211> LENGTH: 45
<212> TYPE: DNA
<213> ORGANISM: Artificial Sequence
<220> FEATURE:
<223> OTHER INFORMATION: Synthetic

<400> SEQUENCE: 33
acatccgcaa ctgtccatac tctgcggaga cagcgcttga agaaa                45

<210> SEQ ID NO 34
<211> LENGTH: 46
<212> TYPE: DNA
<213> ORGANISM: Artificial Sequence
<220> FEATURE:
<223> OTHER INFORMATION: Synthetic

<400> SEQUENCE: 34
agctatgacc atgattacgc caagtactcc tgatgctcaa gggctg               46

<210> SEQ ID NO 35
<211> LENGTH: 46
<212> TYPE: DNA
<213> ORGANISM: Artificial Sequence
<220> FEATURE:
<223> OTHER INFORMATION: Synthetic

<400> SEQUENCE: 35
cttggcgtaa tcatggtcat agcugtttcc tgtgtgaaat tgttat               46

<210> SEQ ID NO 36
<211> LENGTH: 49
<212> TYPE: DNA
<213> ORGANISM: Artificial Sequence
<220> FEATURE:
<223> OTHER INFORMATION: Synthetic

<400> SEQUENCE: 36
cagagtatgg acagttgcgg atguacttca gaaaagatta gatgtctaa            49

<210> SEQ ID NO 37
<211> LENGTH: 45
<212> TYPE: DNA
<213> ORGANISM: Artificial Sequence
<220> FEATURE:
```

<223> OTHER INFORMATION: Synthetic

<400> SEQUENCE: 37
ggggatcttt gacaatttct tgaaactgg cggacattca ttaaa        45

<210> SEQ ID NO 38
<211> LENGTH: 50
<212> TYPE: DNA
<213> ORGANISM: Artificial Sequence
<220> FEATURE:
<223> OTHER INFORMATION: Synthetic

<400> SEQUENCE: 38
aatctttgtt aaaagggtca tggcttttaa tgaatgtccg ccagtttcaa        50

<210> SEQ ID NO 39
<211> LENGTH: 50
<212> TYPE: DNA
<213> ORGANISM: Artificial Sequence
<220> FEATURE:
<223> OTHER INFORMATION: Synthetic

<400> SEQUENCE: 39
agccatgacc cttttaacaa agattcataa ggaaacaggc attgagattc        50

<210> SEQ ID NO 40
<211> LENGTH: 50
<212> TYPE: DNA
<213> ORGANISM: Artificial Sequence
<220> FEATURE:
<223> OTHER INFORMATION: Synthetic

<400> SEQUENCE: 40
ggatgctcaa acaaaaattg ttgcggaatc tcaatgcctg tttccttatg        50

<210> SEQ ID NO 41
<211> LENGTH: 50
<212> TYPE: DNA
<213> ORGANISM: Artificial Sequence
<220> FEATURE:
<223> OTHER INFORMATION: Synthetic

<400> SEQUENCE: 41
cgcaacaatt tttgtttgag catccgacga ttacggctct tgcagaggaa        50

<210> SEQ ID NO 42
<211> LENGTH: 42
<212> TYPE: DNA
<213> ORGANISM: Artificial Sequence
<220> FEATURE:
<223> OTHER INFORMATION: Synthetic

<400> SEQUENCE: 42
ccatcagagc catcagcttc ctctgcaaga gccgtaatcg tc        42

<210> SEQ ID NO 43
<211> LENGTH: 48
<212> TYPE: DNA
<213> ORGANISM: Artificial Sequence
<220> FEATURE:
<223> OTHER INFORMATION: Synthetic

<400> SEQUENCE: 43
ggggatcttt gacaatttcu ttgaaactgg cggacattca ttaaaagc        48

<210> SEQ ID NO 44

-continued

```
<211> LENGTH: 48
<212> TYPE: DNA
<213> ORGANISM: Artificial Sequence
<220> FEATURE:
<223> OTHER INFORMATION: Synthetic

<400> SEQUENCE: 44
ccatcagagc catcagmcttt cctctgcaag agccgtaatc gtcggatg         48

<210> SEQ ID NO 45
<211> LENGTH: 38
<212> TYPE: DNA
<213> ORGANISM: Artificial Sequence
<220> FEATURE:
<223> OTHER INFORMATION: Synthetic

<400> SEQUENCE: 45
agaaattgtc aaagatcccc gccttctcaa cgttcagc                     38

<210> SEQ ID NO 46
<211> LENGTH: 38
<212> TYPE: DNA
<213> ORGANISM: Artificial Sequence
<220> FEATURE:
<223> OTHER INFORMATION: Synthetic

<400> SEQUENCE: 46
gctgatggct ctgatggctt gcaggatgta acgataat                     38

<210> SEQ ID NO 47
<211> LENGTH: 54
<212> TYPE: DNA
<213> ORGANISM: Artificial Sequence
<220> FEATURE:
<223> OTHER INFORMATION: Synthetic

<400> SEQUENCE: 47
ttgagcttcc agtgaagctt ttgtttgaag cgccgacgat cgccggcatt tcag   54

<210> SEQ ID NO 48
<211> LENGTH: 51
<212> TYPE: DNA
<213> ORGANISM: Artificial Sequence
<220> FEATURE:
<223> OTHER INFORMATION: Synthetic

<400> SEQUENCE: 48
cagagccccc gttttcaaa tacgctgaaa tgccggcgat cgtcggcgct t        51

<210> SEQ ID NO 49
<211> LENGTH: 52
<212> TYPE: DNA
<213> ORGANISM: Artificial Sequence
<220> FEATURE:
<223> OTHER INFORMATION: Synthetic

<400> SEQUENCE: 49
ttgagcttcc agtgaagctt ttgtttgaag cgccgacgat cgccggcatt tc      52

<210> SEQ ID NO 50
<211> LENGTH: 52
<212> TYPE: DNA
<213> ORGANISM: Artificial Sequence
<220> FEATURE:
<223> OTHER INFORMATION: Synthetic

<400> SEQUENCE: 50
```
cagagccccc gttttcaaa tacgctgaaa tgccggcgat cgtcggcgct tc    52

<210> SEQ ID NO 51
<211> LENGTH: 46
<212> TYPE: DNA
<213> ORGANISM: Artificial Sequence
<220> FEATURE:
<223> OTHER INFORMATION: Synthetic

<400> SEQUENCE: 51
cgtatttgaa aaacgggggc tctgatggct tgcaggatgt aacgat    46

<210> SEQ ID NO 52
<211> LENGTH: 52
<212> TYPE: DNA
<213> ORGANISM: Artificial Sequence
<220> FEATURE:
<223> OTHER INFORMATION: Synthetic

<400> SEQUENCE: 52
caaacaaaag cttcactgga agctcaatgc ctgtttcctt atgaatcttt gt    52

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
caagtgcctg gttgcgtaca t    21

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
cgcattcgat tactcgcaaa g    21

<210> SEQ ID NO 55
<211> LENGTH: 43
<212> TYPE: DNA
<213> ORGANISM: Artificial Sequence
<220> FEATURE:
<223> OTHER INFORMATION: Synthetic

<400> SEQUENCE: 55
tgagaaggcg gggatctttg acaatttctt tgagatcggc gga    43

<210> SEQ ID NO 56
<211> LENGTH: 46
<212> TYPE: DNA
<213> ORGANISM: Artificial Sequence
<220> FEATURE:
<223> OTHER INFORMATION: Synthetic

<400> SEQUENCE: 56
caacgcttcg acatcacttt ctcagttccg tgtattttgt gtcaca    46

<210> SEQ ID NO 57
<211> LENGTH: 41
<212> TYPE: DNA
<213> ORGANISM: Artificial Sequence
<220> FEATURE:

<223> OTHER INFORMATION: Synthetic

<400> SEQUENCE: 57
gtcaaagatc cccgccttct caacgttcag cacgtcctgc c        41

<210> SEQ ID NO 58
<211> LENGTH: 44
<212> TYPE: DNA
<213> ORGANISM: Artificial Sequence
<220> FEATURE:
<223> OTHER INFORMATION: Synthetic

<400> SEQUENCE: 58
gaaagtgatg tcgaagcgtt gatgaatgtc aatcgggaca atga        44

<210> SEQ ID NO 59
<211> LENGTH: 47
<212> TYPE: DNA
<213> ORGANISM: Artificial Sequence
<220> FEATURE:
<223> OTHER INFORMATION: Synthetic

<400> SEQUENCE: 59
ggctcttgca gaggaagctg augaaattat caaacacggt ttgacgt        47

<210> SEQ ID NO 60
<211> LENGTH: 46
<212> TYPE: DNA
<213> ORGANISM: Artificial Sequence
<220> FEATURE:
<223> OTHER INFORMATION: Synthetic

<400> SEQUENCE: 60
caacgcttcg acatcacttt ctcagttccg tgtattttgt gtcaca        46

<210> SEQ ID NO 61
<211> LENGTH: 45
<212> TYPE: DNA
<213> ORGANISM: Artificial Sequence
<220> FEATURE:
<223> OTHER INFORMATION: Synthetic

<400> SEQUENCE: 61
atcagcttcc tctgcaagag ccgtaatcgt cggatgctca aacaa        45

<210> SEQ ID NO 62
<211> LENGTH: 44
<212> TYPE: DNA
<213> ORGANISM: Artificial Sequence
<220> FEATURE:
<223> OTHER INFORMATION: Synthetic

<400> SEQUENCE: 62
gaaagtgatg tcgaagcgtt gatgaatgtc aatcgggaca atga        44

<210> SEQ ID NO 63
<211> LENGTH: 43
<212> TYPE: DNA
<213> ORGANISM: Artificial Sequence
<220> FEATURE:
<223> OTHER INFORMATION: Synthetic

<400> SEQUENCE: 63
tcataaggaa acaggcattg aggtgccgtt gcgcatcttg ttt        43

<210> SEQ ID NO 64

```
<211> LENGTH: 46
<212> TYPE: DNA
<213> ORGANISM: Artificial Sequence
<220> FEATURE:
<223> OTHER INFORMATION: Synthetic

<400> SEQUENCE: 64
caacgcttcg acatcacttt ctcagttccg tgtattttgt gtcaca            46

<210> SEQ ID NO 65
<211> LENGTH: 46
<212> TYPE: DNA
<213> ORGANISM: Artificial Sequence
<220> FEATURE:
<223> OTHER INFORMATION: Synthetic

<400> SEQUENCE: 65
ctcaatgcct gtttccttat gaatctttgt taaagggtc atggct              46

<210> SEQ ID NO 66
<211> LENGTH: 44
<212> TYPE: DNA
<213> ORGANISM: Artificial Sequence
<220> FEATURE:
<223> OTHER INFORMATION: Synthetic

<400> SEQUENCE: 66
gaaagtgatg tcgaagcgtt gatgaatgtc aatcgggaca atga                44

<210> SEQ ID NO 67
<211> LENGTH: 22
<212> TYPE: DNA
<213> ORGANISM: Artificial Sequence
<220> FEATURE:
<223> OTHER INFORMATION: Synthetic

<400> SEQUENCE: 67
actgaacatg gctgagcatg tg                                        22

<210> SEQ ID NO 68
<211> LENGTH: 26
<212> TYPE: DNA
<213> ORGANISM: Artificial Sequence
<220> FEATURE:
<223> OTHER INFORMATION: Synthetic

<400> SEQUENCE: 68
aagctctcct tccattagaa gaacag                                    26

<210> SEQ ID NO 69
<211> LENGTH: 43
<212> TYPE: DNA
<213> ORGANISM: Artificial Sequence
<220> FEATURE:
<223> OTHER INFORMATION: Synthetic

<400> SEQUENCE: 69
gagaaggcgg ggatctttga caacttcttt atgatcggcg gcc                 43

<210> SEQ ID NO 70
<211> LENGTH: 41
<212> TYPE: DNA
<213> ORGANISM: Artificial Sequence
<220> FEATURE:
<223> OTHER INFORMATION: Synthetic

<400> SEQUENCE: 70
```

```
cctccgagcg caaagaaatc gtcatcaatg ccgatggctt c                          41
```

<210> SEQ ID NO 71
<211> LENGTH: 38
<212> TYPE: DNA
<213> ORGANISM: Artificial Sequence
<220> FEATURE:
<223> OTHER INFORMATION: Synthetic

<400> SEQUENCE: 71

```
gtcaaagatc cccgccttct caacgttcag cacgtcct                              38
```

<210> SEQ ID NO 72
<211> LENGTH: 36
<212> TYPE: DNA
<213> ORGANISM: Artificial Sequence
<220> FEATURE:
<223> OTHER INFORMATION: Synthetic

<400> SEQUENCE: 72

```
gatttctttg cgctcggagg gcattccttg aaggcc                                36
```

<210> SEQ ID NO 73
<211> LENGTH: 5166
<212> TYPE: DNA
<213> ORGANISM: Artificial Sequence
<220> FEATURE:
<223> OTHER INFORMATION: Synthetic

<400> SEQUENCE: 73

```
attatttaca catcgggaac aaccggacgc ccgaaaggcg ttatgatcga gcatcgccag      60
gttcatcatt tggttgaatc tctgcagcag acgatttatc aaagcggcag ccaaaccctg    120
cggatggcat tgcttgcgcc gttccacttt gatgcgtcag tgaagcagat cttcgcgtcg    180
cttcttttgg gccaaaccct ttatatcgta ccgaagaaaa cagtgacgaa cggggccgcc    240
cttactgcat attatcggaa gaacagcatt gaggcgacgg acggaacacc ggctcatttg    300
caaatgctgg cagcagcagg cgattttgaa ggcctaaaac tgaagcacat gctgatcgga    360
ggagaaggcc tgtcatctgt tgttgcggac aagctgctga agctgtttaa agaagccggc    420
acagcgccgc gtttgactaa tgtgtacggg ccgactgaaa cgtgcgttga cgcgtctgtt    480
catccggtta tccctgagaa tgcagttcaa tcagcgtatg tgccgatcgg gaagcgctg    540
gggaataacc gcttatatat tttggatcaa aaaggccggc tgcagcctga aggcgtggcg    600
ggtgagcttt atatcgcggg agacggtgtg ggccgaggct atttacattt gcctgaatta    660
acggaagaga agttttttaca agatccattc gtgccgggcg atcgcatgta ccggaccggg    720
gacgtggtgc gctggcttcc agatggaaca atcgaatatt taggcagaga ggatgaccag    780
gtcaaagtcc gcggataccg gattgagctt ggggaaattg aagccgtgat tcagcaggcg    840
ccagacgttg caaaagccgt tgttttggca cgccctgacg aacagggaaa tcttgaggtt    900
tgcgcatatg ttgtgcagaa gcctggaagc gaatttgcgc cagccggttt gagggagcat    960
gcggccagac agcttcctga ctatatggtg ccggcttact ttacagaagt gacagaaatt   1020
ccgcttacac caagcggcaa agtcgaccgc cgcaagctgt tgcactaga ggtgaaggct    1080
gtcagcggca ctgcctatac agcgccgcga aatgagactg aaaaagcaat cgcagccatt   1140
tggcaggacg tgctgaacgt tgagaaggcg gggatctttg acaacttctt tatgatcggc    1200
ggccattctt tgaaagcgat gatgatgacg gcgaaaattc aagagcattt tcataaggaa    1260
gttccgataa aagtgctttt tgaaaagccg actattcaag aactggcact gtatttggaa   1320
```

```
gagaacgaaa gcaaggagga gcagacgttt gaaccgatca ggcaagcatc ttatcagcag   1380
cattatcctg tatccccggc ccagcggaga atgtatatcc tcaatcagct tggacaagca   1440
aacacaagct acaacgtccc cgctgtactt ctgctggagg gagaagtaga taaagaccgg   1500
cttgaaaacg cgattcagca attaatcaac cggcacgaaa tcctccgtac atcgtttgac   1560
atgatcgacg gagaggttgt gcaaaccgtt cataaaaaca tatcgttcca gctggaggct   1620
gccaagggac gggaagaaga cgcggaagag ataatcaaag catttgttca gccgtttgaa   1680
ttaaaccgcg cgccgctcgt ccgttcgaag cttgtccagc tggaagaaaa acgccacctg   1740
ctgctcattg atatgcatca tattattact gacggaagtt caacaggcat tctaatcggt   1800
gatcttgcca aaatatatca aggcgcagat ctggaactgc cacaaattca ctataaagat   1860
tacgcagttt ggcacaaaga acaaactaat tatcaaaaag atgaggaata ctggctcgat   1920
gtctttaaag gcgaactgcc aatactggat cttcccgcgg atttcgagcg ccagctgaa    1980 cggagctttg cggagagcg cgtgatgttt gggcttgata agcaaatcac ggctcaaatc    2040
aaatcgctca tggcagaaac agatacgaca atgtacatgt ttttgctggc ggcgttcaat   2100
gtactccttt ccaagtacgc gtcacaggat gatatcattg tcggctcgcc gacagctggc   2160
agaacacatc ctgatctgca aggtgtgccg ggtatgtttg tcaacacggt ggcactcaga   2220
acggcaccag cgggagataa aaccttcgcg caattccttg aagaggtcaa aacagccagc   2280
cttcaagcat tcgagcacca gagctatccg cttgaggagc tgattgaaaa gcttccgctt   2340
acaagggata caagcagaag tccgctgttc agcgtgatgt tcaacatgca gaatatggag   2400
attccttcat taagattagg agatttgaag atttcctcgt attccatgct tcatcatgtt   2460
gcgaaatttg atctttcctt ggaagcggtc gagcgtgaag aggatatcgg cctaagcttt   2520
gactatgcga ctgccttgtt taaggacgag acgatccgcc gctggagccg ccactttgtc   2580
aatatcatca aagcggccgc ggctaatccg aacgttcggc tgtctgatgt agatctgctt   2640
tcatctgcag aaacggctgc tttgctagaa gaaagacata tgactcaaat taccgaagca   2700
acctttgcag cacttttga aaaacaggcc cagcaaacac ctgaccattc tgcggtgaag   2760
gctggcggaa atctgttgac ctatcgcgag cttgatgaac aggcgaacca gctggcgcat   2820
catcttcgtg cccaagggc aggaaatgaa gacatcgtcg cgattgttat ggaccggtca   2880
gctgaagtca tggtatccat tctcggtgtc atgaaggcgg gggcagcttt ccttccgatt   2940
gatcctgata cacctgaaga acgaatccgt tattcattag aggacagcgg agcaaaattt   3000
gcggtcgtga atgaaagaaa catgacggct attgggcaat atgaagggat aattgtcagc   3060
cttgatgacg gtaaatggag aaatgaaagc aaggagcgcc catcatccat ttccgggtct   3120
cgcaatcttg catacgtcat ttatacgtcc ggtacgaccg aaaagccaaa gggcgtgcag   3180
attgagcatc gtaatctgac aaactatgtc tcttggttta gtgaagaggc gggcctgacg   3240
aagaggcggg ctgacggaaa tgataagact gtattgcttt catcttacgc atttgacctt   3300
ggctatacga gcatgttccc tgtacttctg gcgggggcg agctccatat cgtccagaag   3360
gaaacctata cggcgccgga tgaaatagcg cactatatca aggagcatgg gatcacttat   3420
atcaagctga caccgtctct gttccataca atagtgaaca ccgccagttt tgcaaaagat   3480
gcgaactttg aatccttgcg cttgatcgtc ttgggaggaa aaaaaatcat cccgactgat   3540
gttatcgcct tccgtaagat gtatggacat accgaattta tcaatcacta cggcccgaca   3600
gaagcaacga tcgcgccat cgccgggcgg gttgatctgt atgagccgga tgcatttgcg   3660
aaacgcccga caatcggacg cccgattgcg aatgccggtg cgcttgtctt aaatgaagca   3720
```

```
ttgaagcttg tgccgcctgg agcgagcgga cagctctata tcacgggaca ggggctcgcg    3780
agagggtatc tcaacaggcc tcagctgaca gccgagagat ttgtagaaaa tccatattcg    3840
ccgggaagcc tcatgtacaa aaccggagat gtcgtacgaa gactttctga cggtacgctt    3900
gcatttatcg gccgggctga tgatcaggtg aaaatccgag gctaccgcat tgagccgaaa    3960
gaaattgaaa cggtcatgct cagcctcagc ggaattcaag aagcggttgt actagcggtt    4020
tccgagggcg gtcttcaaga gctttgcgcg tattatacgt cggatcaaga tattgaaaaa    4080
gcagagctcc ggtaccagct ttccctaaca ctgccgtctc atatgattcc tgctttcttt    4140
gtgcaggttg acgcgattcc gctgacggca aacggaaaaa ccgacagaaa cgctctgccg    4200
aagcctaacg cggcacaatc cggaggcaag gccttggccg caccggagac agcgcttgaa    4260
gaaagtttat gccgcatttg gcagaaaacg cttggcatag aagccatcgg cattgatgac    4320
gatttctttg cgctcggagg gcattccttg aaggccatga ccgccgcgtc ccgcatcaag    4380
aaagagctcg ggattgatct tccagtaaag cttttgtttg aagcgccgac gatcgccggc    4440
atttcagcgt atgtgaaaaa cggggtccc gatggcttgc aggatgtaac gataatgaat    4500
caggatcagg agcagatcat tttcgcattt ccgccggtct tgggctatgg ccttatgtac    4560
caaaatctgt ccagccgctt gccgtcatac aagctgtgcg cctttgattt tattgaggag    4620
gaagaccggc ttgaccgcta tgcggatttg atccagaagc tgcagccgga agggccttta    4680
acattgtttg gatattcagc gggatgcagc ctggcgtttg aagctgcgaa aaagcttgag    4740
ggacaaggcc gtattgttca gcggatcatc atggtcgatt cctataaaaa acaaggtgtc    4800
agtgatctgg acggacgcac ggttgaaagt gatgtcgaag cgttgatgaa tgtcaatcgg    4860
gacaatgaag cgctcaacag cgaagccgtc aaacaaggcc tcaagcaaaa aacacatgcc    4920
ttttactcat actacgtcaa cctgatcagc acaggccagg tgaaagcaga tattgatctg    4980
ttgacttccg gcgctgattt tgacataccg gaatggcttg catcatggga agaagctaca    5040
acaggtgctt accgtatgaa aagaggcttc ggaacacacg cagaaatgct gcagggcgaa    5100
acgctagata ggaatgccgg gattttgctc gaatttctta atacacaaac cgtaacggtt    5160
tcataa                                                                5166
```

```
<210> SEQ ID NO 74
<211> LENGTH: 5
<212> TYPE: PRT
<213> ORGANISM: Artificial Sequence
<220> FEATURE:
<223> OTHER INFORMATION: Synthetic

<400> SEQUENCE: 74

Gly Gly His Ser Leu
1               5
```